United States Patent
You et al.

(10) Patent No.: US 11,123,128 B2
(45) Date of Patent: *Sep. 21, 2021

(54) METHOD AND DEVICE FOR ELECTROCHEMICAL THERAPY OF SKIN AND RELATED SOFT TISSUES

(71) Applicant: THE REGENTS OF THE UNIVERSITY OF CALIFORNIA, Oakland, CA (US)

(72) Inventors: Joon S You, Laguna Niguel, CA (US); Brian Jet-Fei Wong, Irvine, CA (US); Wesley Moy, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 536 days.

This patent is subject to a terminal disclaimer.

(21) Appl. No.: 15/900,985

(22) Filed: Feb. 21, 2018

(65) Prior Publication Data

US 2018/0177543 A1 Jun. 28, 2018

Related U.S. Application Data

(63) Continuation-in-part of application No. 15/841,213, filed on Dec. 13, 2017, now Pat. No. 10,939,950, which is a continuation of application No. 14/280,524, filed on May 16, 2014, now Pat. No. 9,877,770.

(Continued)

(51) Int. Cl.
*A61B 18/12* (2006.01)
*A61B 18/14* (2006.01)
*A61B 18/00* (2006.01)
*A61B 10/02* (2006.01)
*A61N 1/05* (2006.01)
*A61N 1/32* (2006.01)

(52) U.S. Cl.
CPC .......... *A61B 18/1206* (2013.01); *A61B 18/00* (2013.01); *A61B 18/1477* (2013.01); *A61B 10/02* (2013.01); *A61B 2018/0072* (2013.01); *A61B 2018/00452* (2013.01); *A61B 2018/00565* (2013.01); *A61B 2018/00714* (2013.01); *A61B 2018/00761* (2013.01); *A61B 2018/00827* (2013.01); *A61B 2018/00892* (2013.01); *A61B 2018/1425* (2013.01); *A61N 1/0502* (2013.01); *A61N 1/328* (2013.01)

(58) Field of Classification Search
CPC ......... A61B 10/02; A61B 18/00; A61B 18/12; A61B 18/1206; A61B 18/1477; A61B 2018/00452; A61B 2018/00565; A61B 2018/00714; A61B 2018/0072; A61B 2018/00761; A61B 2018/00827; A61B 2018/00892; A61B 2018/1425; A61N 1/0502; A61N 1/328
See application file for complete search history.

(56) References Cited

U.S. PATENT DOCUMENTS

| 7,416,550 B2 | 8/2008 | Protsenko et al. | |
| 2004/0236320 A1* | 11/2004 | Protsenko | A61B 18/14 606/32 |
| 2010/0049031 A1* | 2/2010 | Fruland | A61B 18/16 600/411 |

* cited by examiner

Primary Examiner — Michael F Peffley
Assistant Examiner — Khadijeh A Vahdat
(74) Attorney, Agent, or Firm — Shimokaji IP

(57) ABSTRACT

A method of altering skin tissue includes creating an electrochemical reaction in the tissue, wherein the electrochemical reaction occurs while avoiding electro-thermal damage to the tissue.

21 Claims, 16 Drawing Sheets

Related U.S. Application Data

(60) Provisional application No. 62/462,937, filed on Feb. 24, 2017, provisional application No. 61/824,299, filed on May 16, 2013.

Figure 3C

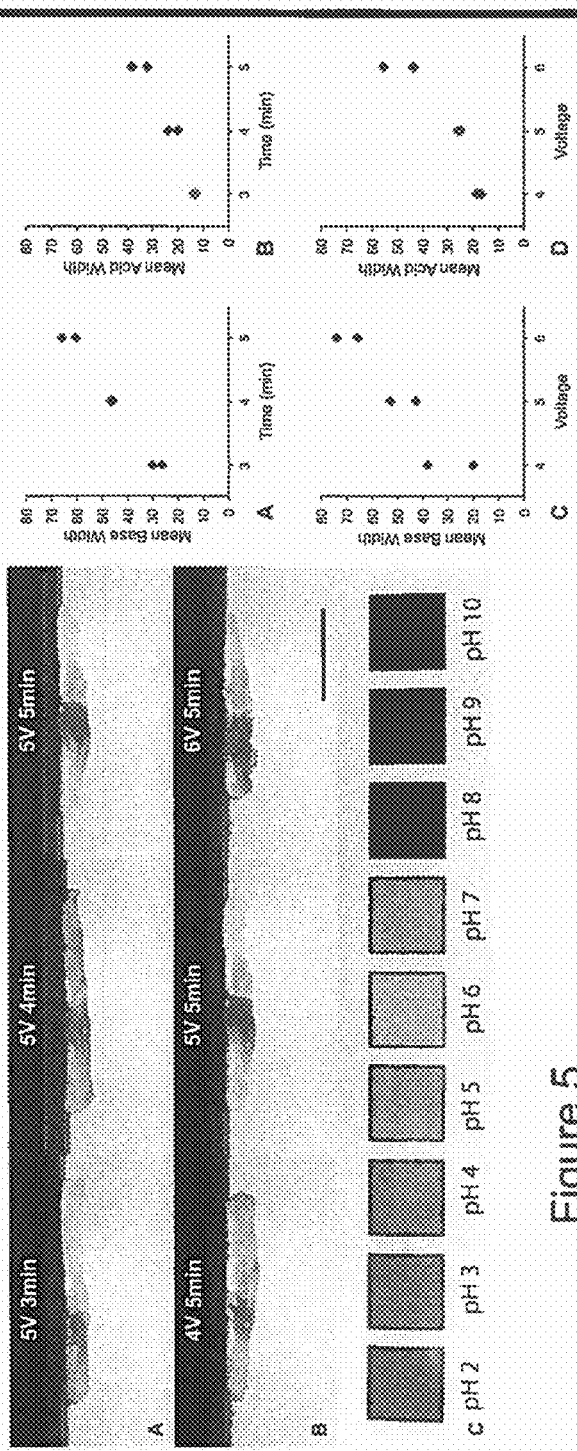
Figure 5
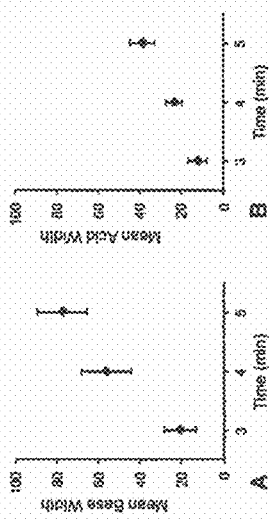
Figure 6
Figure 7

METHOD AND DEVICE FOR ELECTROCHEMICAL THERAPY OF SKIN AND RELATED SOFT TISSUES

CROSS-REFERENCE TO RELATED APPLICATIONS

This application is a continuation-in-part of U.S. patent application Ser. No. 15/841,213 filed Dec. 13, 2017, now U.S. Pat. No. 10,939,950, which is a continuation of U.S. patent application Ser. No. 14/280,524 filed May 16, 2014, now U.S. Pat. No. 9,877,770, both of which claim priority to U.S. provisional application No. 61/824,299 filed May 16, 2013, and all of which are incorporated herein by reference. This application also claims the benefit of U.S. provisional application No. 62/462,937 filed Feb. 24, 2017, which is incorporated herein by reference.

GOVERNMENT RIGHTS

This invention was made with Government support under Grant Nos. 1R21DE019026-01A2 and 1R43DC012258 awarded by the National Institutes of Health and Grant No. DR090349 awarded by the Department of Defense. The Government has certain rights in this invention.

BACKGROUND OF THE INVENTION

The present invention generally relates to the treatment of skin and soft tissue and more, particularly to apparatus and methods of treatment by electrochemical changes.

Currently, regeneration and cosmetic remodeling of human skin tissues is accomplished through one of the following modalities:

Mechanical injuries caused by abrasion of superficial layers of skin ("dermabrasion") or by insertion of microneedles to create small penetrating wounds at multiple sites ("microneedling").

Chemical injuries caused by agents (e.g., weak acids) to remove the superficial and/or deep layers of skin.

Electro-thermal injuries induced by the use of radiofrequency devices. Electrical RF (typically applied at MHz range) induces a thermal injury in the skin and the heat generation is dependent on the tissue electrical resistance and current density. Both capacitive and inductive coupling may be used.

Ultrasonic techniques rely on high frequency mechanical vibrations that alter local skin permeability or rely on the heat generation induced by a highly localized ultrasound.

Light-induced injuries from laser-based devices which may rely on one of the three different types of interactions between light and the tissue:

Opto-thermal effect can be accomplished by absorption of light energy by chromophores (e.g., water) inducing heat generation and resultant tissue remodeling. This may also lead to vaporization of tissue with mass loss (ablation).

Opto-mechanical effect is produced by laser induced mechanical waves within the tissue that can lead to localized stress wave propagation and tissue injury and damage.

Photo-therapy can be achieved by using exogenous or endogenous photochemicals/chromophores that absorb light, which then become activated to lead to cell deaths.

Each of the methods listed above provides distinct benefits and efficacies that are limited for each specific type of treatment. And, as such, none of the current existing technologies provide cure-all capabilities for broad cosmetic applications. They also come with risks of various side-effects, such as exacerbating local injury, pigment change, non-uniform tissue modification (i.e., checker-boarding, depression), nerve injury, hair loss, and texture change.

In general, controlled injuries are created locally via mechanical, chemical, and thermal mechanisms, which are followed by gradual wound healing and a remodeling process to regenerate healthy tissues. Thermal injury is very common for lasers and RF devices, so cooling mechanisms are often needed to reduce any collateral tissue damage. This is due to the non-specific nature of thermal injuries caused by poorly controlled heat transfer. Also, RF and laser devices are in general very expensive relative to classic mechanical modes (i.e., dermabrasion) or chemical modes (i.e., glycolic, trichloroacetic, phenolic acid peels) of treatment.

Prior to the advent of laser and radiofrequency technologies, the most common approach to treat skin texture or contour was dermabrasion or chemical peels. Dermabrasion is simply the use of an abrasive material either handheld or through a mechanical rotary burner to remove the superficial layers of skin. Chemical peeling was pioneered by lay medical practitioners who postulated that the use of the weak acid applied to skin for a short period of time would result in only superficial injuries. In experienced hands, chemical peeling is an extremely low cost way of treating the skin. However, the skill to perform these types of treatments expertly is difficult to acquire, and the complications are significant as it is difficult to ascertain the depth of agent penetration precisely. Skin properties vary substantially, and the absorption of typically used trichloroacetic acid or phenolic acid will vary from region to region; hence a great deal of experience is required to execute this in a reliable and safe fashion.

Prior Use of Lasers

Since the early 90's lasers have grown to become a common tool in a dermatologist's office. Laser skin resurfacing is now commonly used to improve minor facial flaws, such as wrinkles, scars, sun-damages, liver spots, warts, birthmarks, or even oil glands. Lasers are now also used to remove unwanted hair, acnes and acne-related scars. In laser skin resurfacing, short pulse infrared laser is delivered to create a highly controlled superficial ablation of skin. Skin resurfacing works like chemical peels, but due to the interaction being defined by the distribution of light, outcomes are more reproducible and straightforward. The downside of this technology, however, is that it still relies upon non-specific thermal injuries, and thus significant postsurgical redness could persist for up to six months following treatments. Secondly, this technique is not immune to major scarring just like chemical peels. Recently, development of fractional laser technology has enabled better outcomes for laser skin resurfacing. In the fractional method, laser energy is delivered to the skin in a checkerboard pattern, which results in regions of normal tissue interspersed between areas where full laser ablation occurred. However, fractional laser is still somewhat difficult to control in individuals who have olive complexion which is the vast majority of the world's population.

Prior Use of Needle Electrodes

Microneedle rollers have been used for over a century for reduction and modification of cutaneous scars. The latest microneedle therapy utilizes a mechanical pen-type device to rapidly insert an array of needles into the skin to a pre-defined and controlled depth. In typical microneedle treatments, the small and localized puncture wounds created by the microneedles are gradually filled in with new epithelial cells that migrate from adjacent healthy tissues.

In RF therapy, radiofrequency current is delivered to the skin to generate heat. A typical RF device for skin treatment delivers hundreds of volts of AC electrical current at high frequencies (i.e., 5 MHz) with energy output of 50 W. Radiofrequency energy is coupled to the skin in a capacitive manner, which causes generation of heat in a region defined by the local electric field. Collateral damage to the skin structure and cells may be reduced with the use of cooling techniques that can reduce the temperature by 4-5 degrees, and by selection of needle geometry and dosimetry. There are devices which use contact electrodes as well as needle electrode arrays that can deliver RF electrical energy to the skin. Delivery of RF in a form of needle array allows treatment of both the superficial and sub-surface tissues through combination of needle penetration depth and electrical energy delivered in the form of heat. Thus, the combination of electrothermal treatment (i.e., RF) with a micro electrode needle array puncturing potentially achieves both shallow and deep tissue (dermal) damages which then induce tissue regeneration. Microneedles can be coupled with RF technology to produce more localized thermal injuries and there have been a few commercial systems introduced into the market recently.

Prior Irreversible Electroporation

Recently, a new form of tumor ablation called irreversible electroporation (IRE) has been developed and is undergoing clinical studies. IRE is a non-thermal tumor ablation technique that uses pulsed direct electric current of 20-50 A at 500-3000V to create electroporation of membranes, which induce cell death while structural integrity of tissues remain. IRE selectively ablates the cells and leaves the extracellular structures and can be used to create natural tissue scaffolding.

Prior Electrochemistry of Cancer

Earliest reported direct application of electrochemistry for human tissue was to destroy cancer tissues. Long, large gauge needles were inserted into solid organs such as the liver and then DC currents were delivered to destroy cancer and surrounding tissues for multiple hours. Recently, the same approach has been applied to destroy cancer cells that are not easily accessible due to a presence of another organ.

Prior Electromechanical Reshaping

A most recent application of electrochemistry has been focused on reshaping of cartilage tissues. In this method called Electromechanical Reshaping (EMR), a mechanical stress is established on a tissue structure (i.e., cartilage), and then needle electrodes are inserted in the region of stress concentration. Upon delivery of electrical current at a fixed voltage (typically 3-24 volts), resultant electrochemistry induces re-alignment of chemical bonds while the mechanical stress applied externally allows reshaping of the overall tissue structures to desired shapes. Unlike the electroporation, the objective of EMR is to induce electrochemical changes in tissue, with the aim of directly altering macroscopic changes in stress-strain relationships. EMR was conceived as a means to alter tissue mechanics in cartilage, tendon, ligament, cornea, and related tissues that were either load bearing or structural in nature. It must be emphasized that the objectives of the EMR are on changing the shape of an existing structure, and collateral damages incurred on the skin tissues were considered side-effects caused by incidental contact of the needle electrode with skin and subcutaneous tissue.

As can be seen, there is a need for improved apparatus and methods for the treatment and/or shaping of skin tissue.

SUMMARY OF THE INVENTION

In one aspect of the present invention, a method of altering skin tissue comprises creating an electrochemical reaction in the tissue; wherein the electrochemical reaction occurs while avoiding thermal damage to the tissue.

In another aspect of the present invention, a method of altering skin tissue comprises using at least an anodic electrode and a cathodic electrode in the tissue to initiate an electrochemical reaction in the tissue; and limiting a change in temperature of the tissue to avoid thermal damage to the tissue.

In a further aspect of the present invention, a method of altering skin tissue comprises mechanically disrupting the tissue; electrochemically degrading the tissue; and minimizing a potential for thermal damage to the tissue.

In a still further aspect of the present invention, a method of altering skin tissue comprises electrochemically generating sodium hydroxide, hydrogen gas, and either chlorine gas or oxygen gas at the tissue; electrochemically forming acid/base species at the tissue; and limiting a temperature change of the tissue during electrochemically generating and electrochemically forming.

In an additional aspect of the present invention, apparatus for altering skin tissue comprises an electronic system configured to cause an electrochemical reaction in the tissue; and wherein the electronic system is further configured to avoid thermal damage to the tissue.

In yet another aspect of the present invention, apparatus for altering skin tissue comprises at least two electrodes configured to cause an electrochemical reaction in the tissue; and a controller in communication with the electrodes and configured to create an electrical potential across the electrodes; cause an oxidation reaction spatially distinct in the tissue from a reduction reaction; and limit a temperature change in the tissue.

Herein, the terms "altering", "altered" or the like in the context of methods and apparatus of the present invention are intended to broadly mean, for example, affecting healthy and/or unhealthy tissue, and changing healthy and/or unhealthy tissue. As a further example, "altering", "altered" or the like may, for example, include treating, removing, degrading, damaging, absorbing, modifying, shaping, and/or sculpting tissue.

Various embodiments herein include a method of modifying a tissue, comprising providing an electrochemical interaction in a tissue, and modifying the tissue by exploiting the electrochemical interaction. In another embodiment, exploiting the electrochemical interaction comprises utilizing an electrochemical potentiostat to apply a specific electrical potential to an array of electrodes. In another embodiment, the electrodes are one or more needle electrodes inserted into the tissue. In another embodiment, exploiting the electrochemical interaction comprises potential-driven electrochemical modification of tissue (PDEMT). In another embodiment, the electrochemical interaction is optimized based on the identification and isolation of one or more discrete electrochemical reactions that cause shape change of the tissue. In another embodiment, the electrochemical interaction is optimized based on specific electrical dosimetry, electrode placement, and/or type of composition. In another embodiment, the tissue comprises a charged polymer hydrogel. In another embodiment, the tissue comprises skin tissue. In another embodiment, modifying the tissue comprises changing the physical shape of the tissue. In another embodiment, modifying the tissue comprises changing physical properties. In another embodiment, changing physical properties includes mechanical behavior-static and dynamic, electrical behavior, optical properties, and/or thermal properties. In another embodiment, modifying the tissue comprises changing biological behavior. In another embodiment, changing biological behavior includes shape change of the tissue, appearance of the tissue, and/or altering drug delivery properties of the tissue. In another embodiment, modification of the tissue is a part of an overall drug treatment regimen. In another embodiment, the modification of tissue is performed in tandem with one or more defined changes in mechanical state in tissue, temperature of tissue, pressure, compression, and/or atmospheric and ambient conditions. In another embodiment, exploiting the electrochemical interaction in the subject comprises use of a system comprising one or more electrodes and a control system to apply a precise electrical potential.

Other embodiments include a method of treating a disease and/or condition in a subject, comprising defining an electrochemical interaction in a constituent of a tissue in a subject, and treating the disease and/or condition by exploiting the electrochemical interaction in the subject. In another embodiment, exploiting the electrochemical interaction results in altering the constituent of living tissue. In another embodiment, the constituent is skin tissue. In another embodiment, treating the disease and/or condition is the treatment of one or more biologic contaminants. In another embodiment, the one or more biologic contaminants include bacteria, fungi, molds, and/or viruses. In another embodiment, exploiting the electrochemical interaction in the subject comprises potential-driven electrochemical modification of tissue (PDEMT). In another embodiment, the subject is a human. In another embodiment, exploiting the electrochemical interaction in the subject further comprises placement of cathode and anode electrodes in an effective geometric arrangement. In another embodiment, modification of the tissue is part of an overall drug treatment regimen. In another embodiment, the modification of tissue is performed in tandem with one or more defined changes in mechanical state in tissue, temperature of tissue, pressure, compression, and/or atmospheric and ambient conditions. In another embodiment, exploiting the electrochemical interaction in the subject comprises use of a system comprising one or more electrodes and a control system to apply a precise electrical potential.

Other embodiments include a system for exploiting an electrochemical interaction in a subject, comprising one or more electrodes, and a control system to apply a precise electrical potential. In another embodiment, the control system utilizes a potentiostatic control. In another embodiment, the control system utilizes a galvanostatic control. In another embodiment, the control system utilizes operation amplifiers. In another embodiment, the control system further comprises a feedback control. In another embodiment, the feedback control comprises monitoring tissue effect, change in mechanical properties, electrical properties, or optical properties, and total charge transfer. In another embodiment, the feedback control comprises a measure and control of current, potential, charge transfer, pH, concentration of species generated by the system, and/or evolution of gases. In another embodiment, the one or more electrodes comprises a working, reference, and auxiliary electrode, or a cathode electrode and an anode electrode. In another embodiment, the one or more electrodes have a static placement. In another embodiment, the one or more electrodes are within a flow through cell. In another embodiment, the one or more electrodes have a shape that is needle, flat plate, curved, clamshell, complex, screen, foam, solid-stiff, soft, pliant, moldable, conforming, and/or liquid. In another embodiment, the one or more electrodes are made from platinum, iridium, and/or graphite. In another embodiment, the one or more electrodes are coated with a plurality of oxidation catalysts. In another embodiment, the one or more electrodes comprise sequestered auxiliary electrodes in an isolated chamber connected by a salt bridge and/or luggin capillary. In another embodiment, the one or more electrodes are a reference electrode. In another embodiment, the one or more electrodes are composed of base metals and electro-plated. In another embodiment, the applied precise electrical potential is modulated. In another embodiment, the applied precise electrical potential is modulated by pulsed, complex or simple waveform, and/or on and off cycles. In another embodiment, the control system is adapted for use in conjunction with open surgery, endoscopic delivery, percutaneous, transmucosal, in an air environment, in an aqueous environment, image guided therapies to target specific tissues and/or targets, biopsy, and/or tissue sampling. In another embodiment, the control system is used in tandem with one or more of the following: agents that activate a pro-genic drug, user created changes in tissue composition, injectable drugs, agents that produce cross-linking of proteins, agents that alter pH, activate a catalyst for tissue effects, osmotically active agents, saline solutions, buffers, reactive oxygen scavengers, and chemicals that alter electrochemistry of the system. In another embodiment, the system further comprises a plurality of set of electrodes. In another embodiment, the plurality of set of electrodes are used simultaneously or at different times. In another embodiment, the plurality of set of electrodes are used at the same location or spaced apart. In another embodiment, the plurality of set of electrodes are in a multiplexing arrangement of the specific chemical reaction desired. In another embodiment, the system further comprises using an electrochemistry reaction to generate an active polymerization catalyst. In another embodiment, the system further comprises polymerization of polyanaline, polypyrrole, and/or polythiophene.

Various embodiments include a method of shaping skin tissue in a patient, comprising providing a potential-driven electrochemical modification of skin tissue (PDEMT) device, and using the device to shape skin tissue in the patient. In another embodiment, skin tissue is shaped by water electrolysis that results in protonation of fixed negative charges. In another embodiment, the method further comprises increasing tissue viability by minimizing pH gradients and/or ROS generation. In another embodiment, the device incorporates bipotentiostat and/or polypotentiostat technology.

Other embodiments include a method of treating a skin tissue malformation condition in a patient, comprising providing a potential-driven electrochemical modification of tissue (PDEMT) device, and treating the patient by using the device to treat skin tissue. In another embodiment, the device incorporates bipotentiostat and/or polypotentiostat technology.

Other embodiments include an apparatus, comprising a potential-driven electrochemical modification of tissue (PDEMT) device adapted for shaping skin tissue in a patient.

In another embodiment, the device incorporates bipotentiostat and/or polypotentiostat technology.

These and other features, aspects and advantages of the present invention will become better understood with reference to the following drawings, description and claims.

BRIEF DESCRIPTION OF THE DRAWINGS

Exemplary embodiments are illustrated in referenced figures. It is intended that the embodiments and figures disclosed herein are to be considered illustrative rather than restrictive.

FIG. 3C is a screenshot of a user interface that may be part of the system in FIG. 3A.

FIG. 5 are pictures of tissue after ECT in accordance with embodiments of the present invention.

FIG. 6 are graphs of ECT effect versus time and voltage in accordance with embodiments of the present invention.

FIG. 7 are graphs of ECT effect versus time in accordance with embodiments of the present invention.

DETAILED DESCRIPTION OF THE INVENTION

Figure 1:
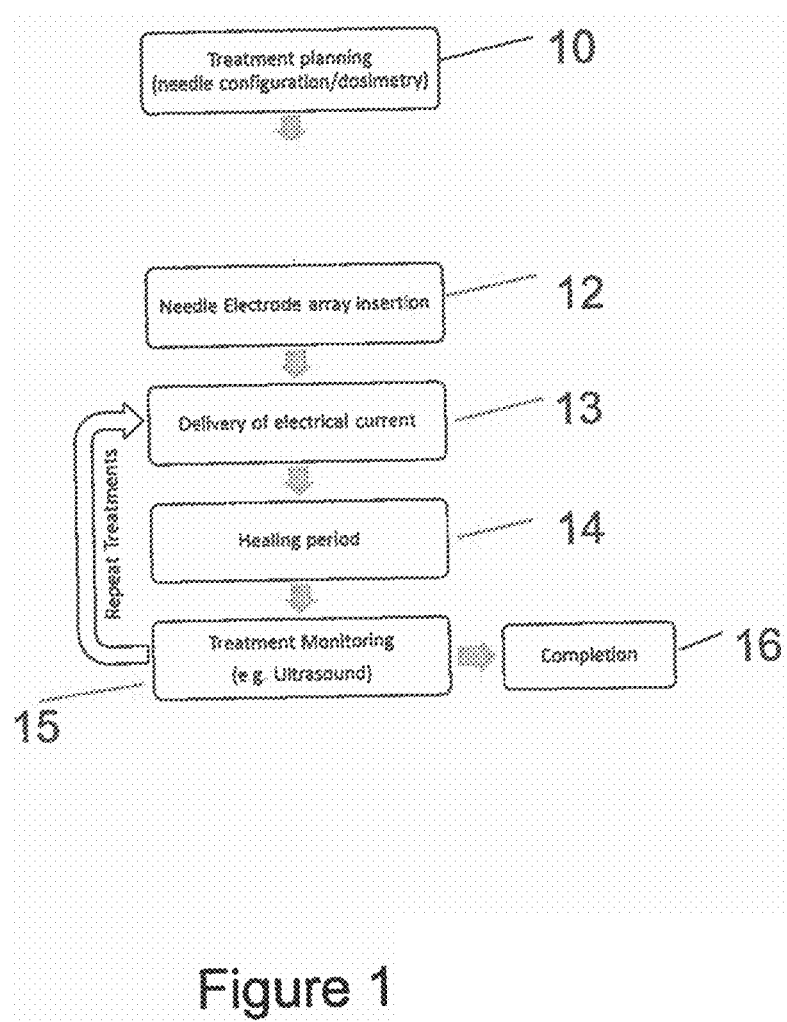
FIG. 1 is a flow chart depicting a method of electrochemical treatment (ECT) of skin tissue in accordance with an embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features. However, any single inventive feature may not address any of the problems discussed above or may only address one of the problems discussed above. Further, one or more of the problems discussed above may not be fully addressed by any of the features described below.

All references cited herein are incorporated by reference in their entirety as though fully set forth herein. Unless defined otherwise, technical and scientific terms used herein have the same meaning as commonly understood by one of ordinary skill in the art to which this invention belongs. Singleton et al., Dictionary of Microbiology and Molecular Biology 4th ed., J. Wiley & Sons (New York, N.Y. 2012); March, Advanced Organic Chemistry Reactions, Mechanisms and Structure 5th ed., J. Wiley & Sons (New York, N.Y. 2001); and Sambrook and Russel, Molecular Cloning: A Laboratory Manual 4th ed., Cold Spring Harbor Laboratory Press (Cold Spring Harbor, N.Y. 2012) provide one skilled in the art with a general guide to many of the terms used in the present application. One skilled in the art will recognize many methods and materials similar or equivalent to those described herein, which could be used in the practice of the present invention. Indeed, the present invention is in no way limited to the methods and materials described.

As used herein, the abbreviation "PDEMT" refers to potential driven electrochemical modification of tissue.

As used herein, the abbreviation of "ECT" means electrochemical treatment which can incorporate one or more aspects of PDMET.

Broadly, the present invention provides methods and apparatus for, among other things, dermatology and cosmetic treatments; skin rejuvenation through wrinkle removal or skin textural and subtle contour changes, and scar tissue reduction therapy. The present invention employs the electrochemical treatment (ECT) of skin tissue and related soft tissues.

This invention can be used for permanent hair removal, sweat gland inactivation, which are results of side effects of the skin ECT treatment. This invention is different from the conventional hair electrolysis, in which electrodes are used non-invasively (no penetration into skin). Electrochemical damages done directly to the hair follicles through subcutaneous needle electrodes will likely cause more permanent hair loss than the conventional electrolysis.

This invention can also be used in combination with drug delivery to either prevent anomalous collagen structures (i.e., scars) or to loosen the large area scars that are often responsible for skin contractures leading to limited mechanical mobility. In this case, the electrochemical therapy induces loosening of collagen structures leading to easier diffusion of drugs or biological materials into deeper tissue layers. This is particularly helpful in scar treatments as the scars tend to form denser collagen structures than those in the normal skin. The invention can be particularly useful in treating large area scars (i.e., burn scars) that often cause functional problems through collagen contractions. Presently, fractional laser ablation is used to accomplish this task, albeit at major expense to the patient.

This invention generally works by inserting very small, narrow diameter needles or needle arrays into the skin. Needles are passivated (high redox potential) so no metallic species are generated. The needles are connected to a battery or similar DC electrical power source. Low voltage (e.g., about 3 to about 9V) and low current (e.g., about 1 to about 2 mA between each anode-cathode pair) is used, and the needles do not heat up or get warm (e.g., less than 1-2° C. on the needle surface). In fact, watch batteries are more than adequate to create electrochemical reactions within skin.

When electricity flows into biological tissues such as skin, many chemical reactions can occur, but "splitting" water into oxygen and hydrogen is a major reaction. As a byproduct, natural acids and bases are generated in the skin, and because the needles are very small and because the electricity is delivered for only a short time (e.g., about 1 to about 5 min), this only happens in the immediate vicinity (e.g., about 1 to about 3 mm) of the needles. The generation of acid or base gradients causes changes in the skin, and then creates a low-grade injury, which subsequently triggers tissue regeneration, eventually leading to tightening and texture changes.

Generally, in this invention, the chemical reactions around the needles result in the production of hydrogen gas (at the cathode) and oxygen gas (at the anode). These reactions also raise and lower the pH in vicinity of the respective electrodes.

This invention may be ideal for hypertrophic skin or traumatic scar treatment when skin contracture causes functional problems in patients. Also, this invention can be particularly useful for creating subtle contour changes in skin through localized 3-dimensional skin injuries. Three-dimensional contouring can be achieved through a combination of (i) control of the penetration depth of the active conductive surface of the electrode, (ii) the 2-dimensional array needle configuration (density and size), and (iii) the 2-dimensional dosage configuration (i.e., individually controlled needle electrode).

This invention can also be used in combination with drug therapy to enhance the effect of drug injection (needles) or diffusion (creams/topicals) into deeper skin layers. In general, the embodiments of the ECT devices can have a capability of precisely controlling and limiting the amount of electrical charge delivered to the tissues.

One embodiment may include a closed-feedback loop DC power controller that can deliver constant voltage or/and constant current at multiple voltage levels (e.g., 5V, 6V, 7V, 8V) and simultaneously monitor the current flow through the tissue for multiple anode-cathode combinations. Another embodiment may utilize potential driven electrochemical cells.

By employing a conventional potentiostat—an electrical circuit based on an inexpensive operational amplifier—to control the electric fields, it is possible to monitor and control precisely the quantities of acids and bases produced. By enabling control over the applied voltages, the potentiostat allows selection of specific electrochemical reactions with tight spatial resolution. Both acids and bases can hydrolyze or otherwise chemically modify skin molecules. Later on, hydrolyzed skin molecules are absorbed by the body, and the region treated assumes a better appearance.

In this invention, no external mechanical stress must be applied for the treatment, though this may be optional. The exact mechanism achieved by the present invention is unclear at the moment. But it may be likely that the electrochemical denaturation of the collagen structures in combination with the mechanical puncture wounds, in synergy, trigger more comprehensive tissue regeneration involving both superficial and deep skin tissues. Herein, the novel, electrochemical reactions of biochemical molecules may form skin structures (i.e., proteoglycans, collagen, and lipids).

The present invention not only relies on (a) the insertion of needles (multiple microneedles) into the skin at precise depths but also (b) the delivery of a DC electrical potential at constant or variable amplitudes (stepped, not alternating) while operating at much lower frequencies (e.g., about 1 Hz to about 10 kHz) than RF so as not to induce thermal effect or damage. In other words, the present invention avoids thermal damage and/or minimizes a potential for thermal damage. This can be accomplished by, among other things, limiting a change in temperature of the tissue, limiting a voltage amount while applying the electrical potential, limiting an electrical current amount while applying the electrical potential, and limiting a time of applying the electrical potential. Accordingly, the present invention utilizes the electrochemical reactions to achieve a controlled degradation of underlying collagen structures and subsequent native remodeling of sub-epidermal layers of the skin to result in healthy skin tissues.

While the present invention may use needle systems inserted into the skin like RF devices, rather than generating heat to denature the connective tissues from RF devices, the present invention utilizes potential or voltage differences to drive electrochemical reactions that produce H+ and OH−, which then diffuse down both a concentration gradient and electric field into the tissue. This results in the generation of electrochemical changes with no/minimal heat generation (e.g., about 1 to about 2° C. tissue change).

Moreover, the mechanisms of action are entirely different between the electro-thermal vs. electro-chemical modes. In electro-thermal methods, local tissue heating contracts and thickens collagen fibers, and subsequently disrupts chemical bonds which, in turn, weakens collagen structures and initiates wound-healing processes; or excessive heating can also result in pyrolysis.

On the other hand, the electrochemical method described in this invention achieves tissue change without generating any significant local heat, and instead drives electrochemical reactions without the risks or side effects caused by electro-thermal methods. The disclosed invention does not rely on thermal coagulation, but initiates biochemical modifications of collagen and other structural macromolecules through electrical energy (i.e., electrolysis of water and resultant pH change as well as focal concentration of free electrolytes). Electrochemical therapy herein may rely on major modification of higher level structural elements (i.e., tertiary/quaternary bonds) through changes of local pH level, while electro-thermal methods completely denature the collagen structures through heating.

Accordingly, an object of the present invention is to alter matrix structure and possibly modify cellular behaviors to trigger long-term focal remodeling of the tissue, particularly in skin and subcutaneous tissues. It creates electrochemical reactions in the region surrounding the needles, which would lead to the generation of changes in pH gradients through hydrolysis. Other electrochemical species may be generated at the same time including the evolution of chlorine gas, and possibly even the oxidation or reduction of organic molecules in the tissue matrix.

One of the unique advantages of this invention is that electrochemical changes in tissue can be safely generated while being highly localized to specific areas and depths. Spatial selectivity can be achieved by the precise placement of specially designed needles combined with the spatial variation in electric field geometry. Duration of electricity application, and the selection of either an anodic or cathodic reaction, also contribute to achieving specifically desired clinical/cosmetic outcomes. Spatial control can be easily customized through electrode composition, needle design, placement, and electrical dosimetry. Control of the rate of electrochemistry can also be achieved through selection of electrical potential. In principle, ECT is capable of contouring of skin tissues below mm spatial scale through combined control of needle configuration, electrical dosimetry and targeted specific electrochemical reactants. Unlike the simple microneedles or RF-microneedles, the current invention has the potential capability of creating micro-contoured damages in 3-dimensional skin structures.

Often the subtle differences in underlying skin tissues can create visibly cosmetic blemishes. Most prior arts have focused on creating nonspecific 2-dimensional injuries and, in general, lack the capability of creating very subtle contour changes. In many cases, multiple treatments are required for achieving desired cosmetic outcomes. In some cases, scarring can be too extensive and lead to negative cosmetic outcomes. Potentially, laser therapy could be used to create precise injuries in subsurface tissues, but the practical implementation would require expensive 3-dimensional mechanical control system along with high end optics (i.e. microscope).

In this invention, spatial control of the 3-dimensional injuries can be achieved by highly localized and easily manageable dosimetry of electrochemical reactions surrounding the electrode needles. For example, the arrangement between the number of anodes vs. cathodes and spatial distribution among the pair(s) of electrodes allows customized treatment schemes in 2-dimensional arrays of microneedles. Also 2-dimensional mapping of varying dosages can be achieved based on voltages and currents by addressing specific cathodes and anodes.

In addition to 2-dimensional spatial arrays, the treatment depths can be also customized by controlling the depth of the needle penetration in combination with the use of needles with specific conductive areas along the shaft of the needle electrode. Thus, 3-dimensional injuries can be delivered within skin tissue, which can then lead to very subtle changes in the skin texture and contour.

The present needle-based technology combines the placement of specialized needles or needle arrays and their insertion into the skin. The needles can be specially designed to allow precise penetration into the skin with components of the needle insulated to isolate the surrounding tissue layers from the electrochemical damage. Once the electrodes are placed in the skin or soft tissue, direct current is applied. The electrical potential can then be adjusted in a stepwise or continuous fashion; these changes are orders of magnitude (e.g., about 10 to about 1000 times) below the modulation rate at RF frequencies which are in MHz regime.

FIG. 1 is a flow chart of an exemplary method of electrochemical treatment (ECT) of skin tissue according to the present invention. In an embodiment, a step 10 may include treatment planning 10, a step 12 may include inserting electrode needles into the tissue, a step 13 may include delivering an electric current to the electrodes, a step 14 may include allowing the tissue to heal, a step 15 may include monitoring the healing process, and a step 16 may include the completion of healing.

Figure 2A:
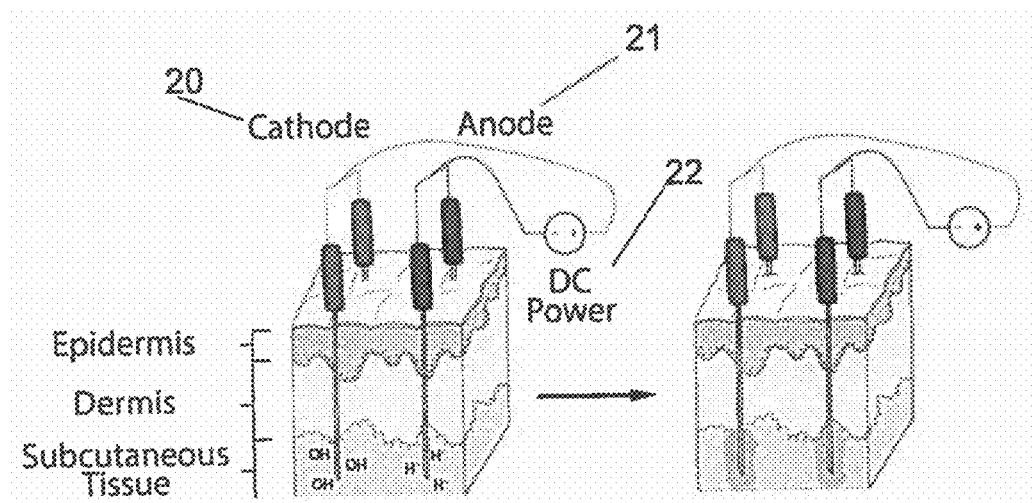
FIG. 2A is a schematic diagram of apparatus for ECT in accordance with an embodiment of the present invention.

FIG. 2A is a schematic diagram of exemplary apparatus that may be employed in a system for carrying out a method of ECT according to the present invention. In an embodiment, two pairs of cathodes (20) and anodes (21) are configured in an array and electrically driven by a DC power supply 22.

Figure 2B:
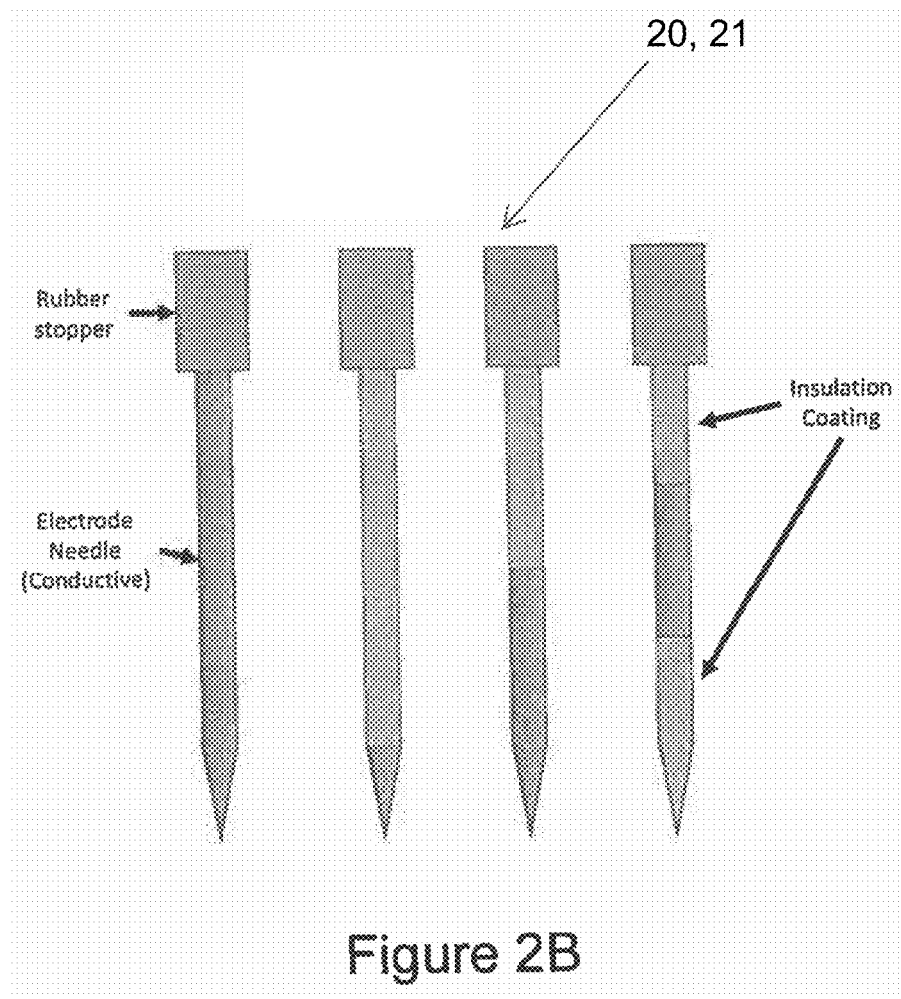
FIG. 2B are schematic side views of electrodes that may be employed in the apparatus of FIG. 2A.

FIG. 2B are schematic side views of electrodes that may be employed in the apparatus of FIG. 2A. According to these exemplary embodiments, the electrode needle can be insulated at different portion(s) thereof to protect certain parts of the tissue. At the same time, insulation coatings of the electrode needle shaft can be used to create conductive regions and non-conductive regions at various depths of the skin.

In one embodiment, the entire needle may be insulated except at its distal tip. That can provide protection of the epidermis and dermis layers. The non-insulated distal or conductive end of the electrode can extend into the subcutaneous tissue to enable electrochemical reactions therein. In another embodiment, the needle may be insulated at only its upper half. In a further embodiment, the needle may be insulated except at the mid portion thereof.

Figure 2C:
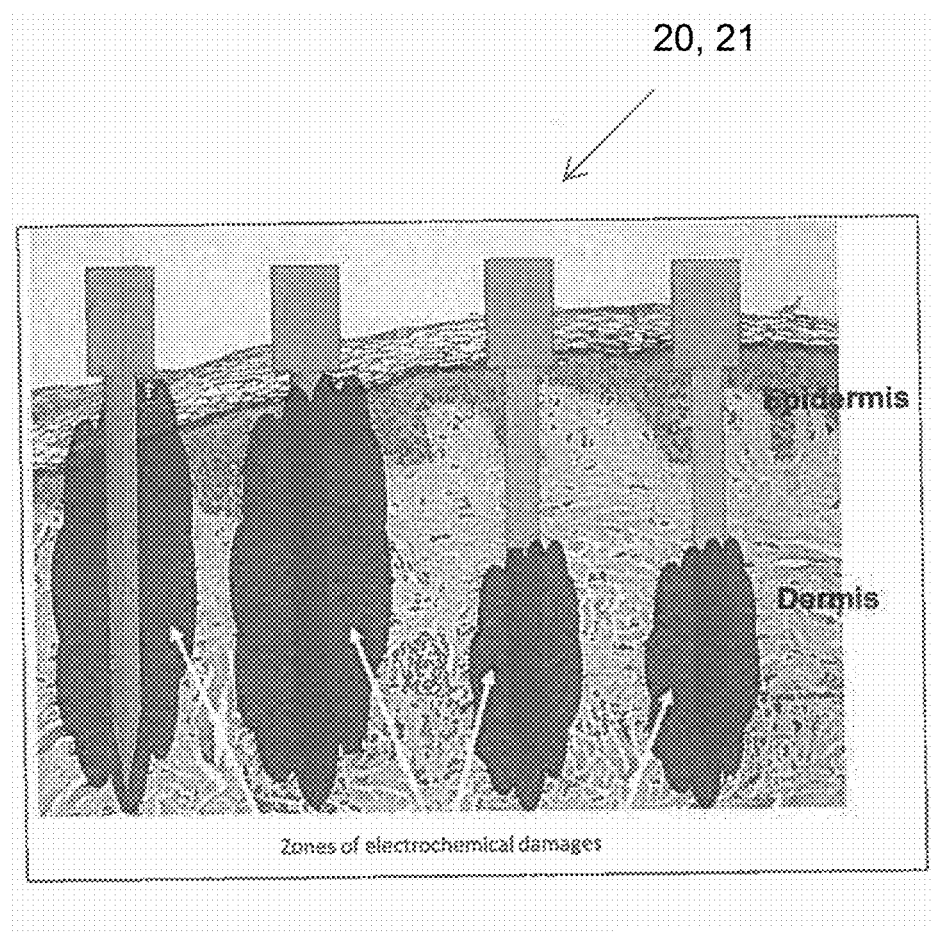
FIG. 2C is a schematic diagram of electrodes and electrochemical changes that may be employed in the apparatus of FIG. 2A.

FIG. 2C are schematic side views of exemplary electrochemical reactions in tissue that may be achieved by the apparatus of FIG. 2A. These reactions can drive pH change in the vicinity of the non-insulated portions of the electrodes to create localized, low-grade disruption, degradation, and/or damage to the tissue at various depths. For example, in FIG. 2C, the two electrodes on the left are not insulated and therefore create zones of electrochemical damage or tissue change that extend along and around the entire needle (other than where a rubber stopper may be located as shown in FIG. 2B). In contrast, the two electrodes on the right are insulated at their upper portions and, therefore, the zones of electrochemical damage or tissue extend along and around the lower portions of the needles.

Figure 2D:
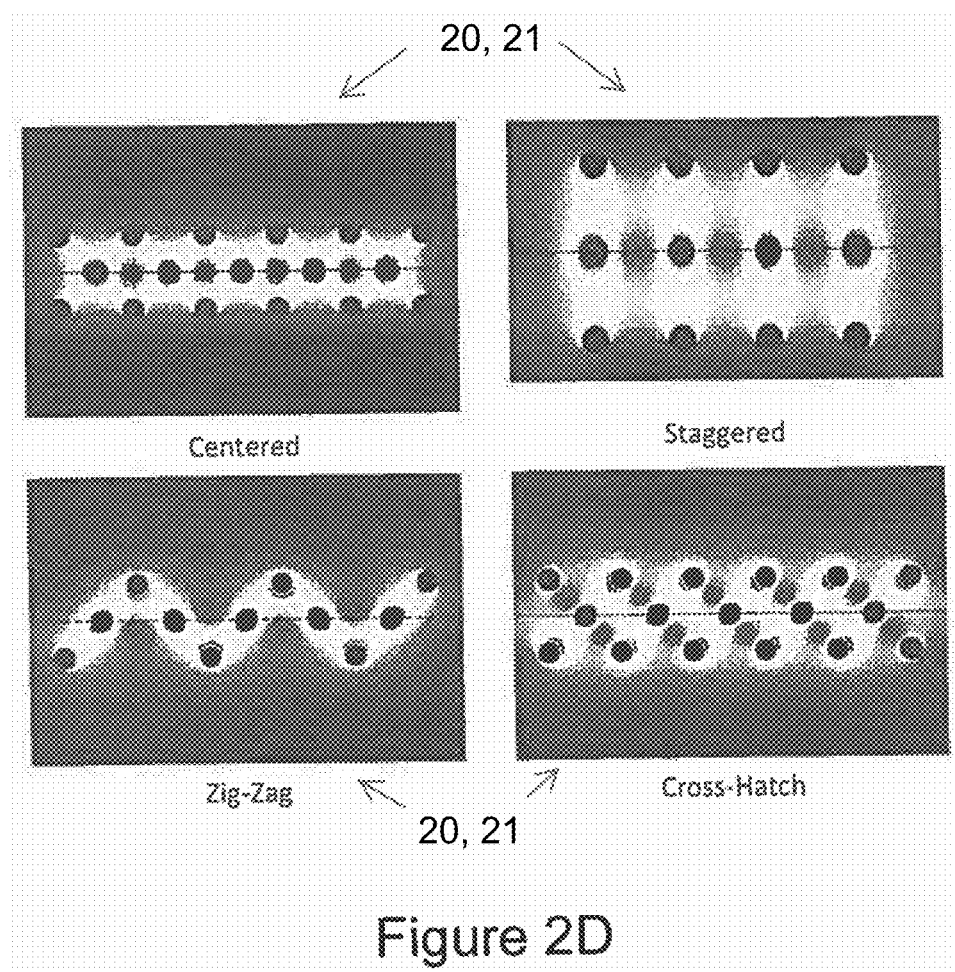
FIG. 2D are images of electrode arrays that may be employed in the apparatus of FIG. 2A.

FIG. 2D are top end views of images of exemplary electrode arrays that may be employed in the apparatus of FIG. 2A. As shown, the number of electrodes may vary, and the electrodes may be provided in different configurations or arrays. The dark circles are electrode needles while the lighter areas around the dark circles depict electric fields of the electrodes.

Figure 2E:
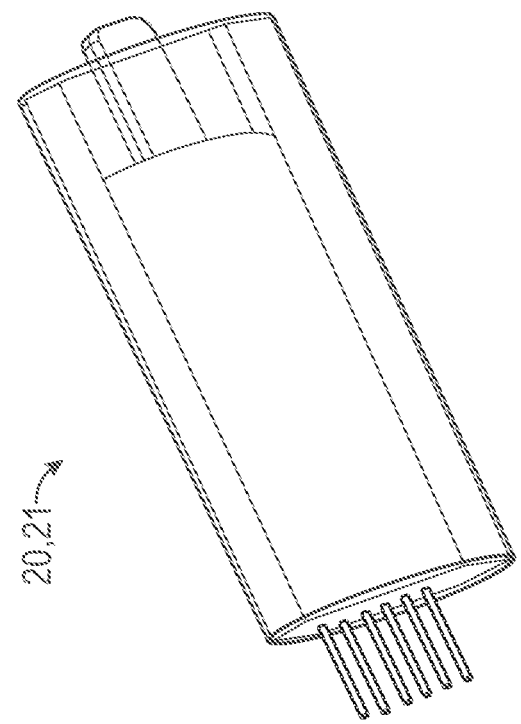
FIG. 2E are pictures of electrode cartridges that may be employed in the apparatus of FIG. 2A.
Figure 2E:
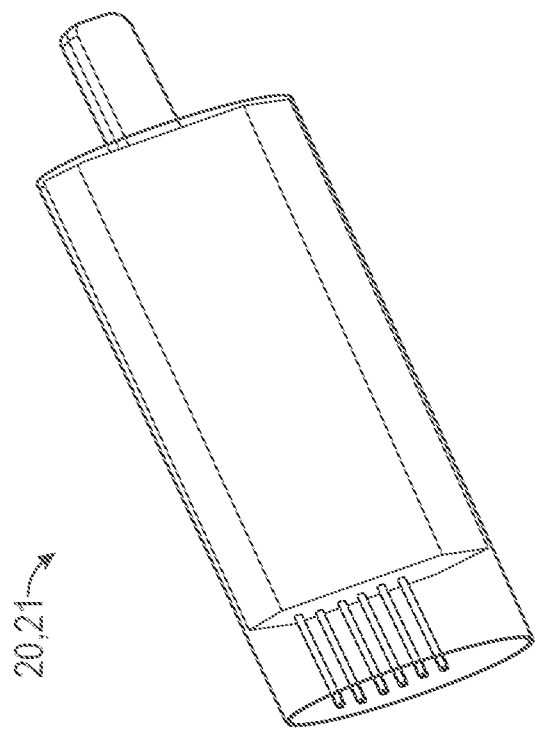

FIG. 2E are pictures of electrode cartridges that may be employed in the apparatus of FIG. 2A. In embodiments as shown, the needle arrays can be designed as disposable units with the array unit being mounted inside a cylindrical tube for mechanical actuation.

Figure 2F:
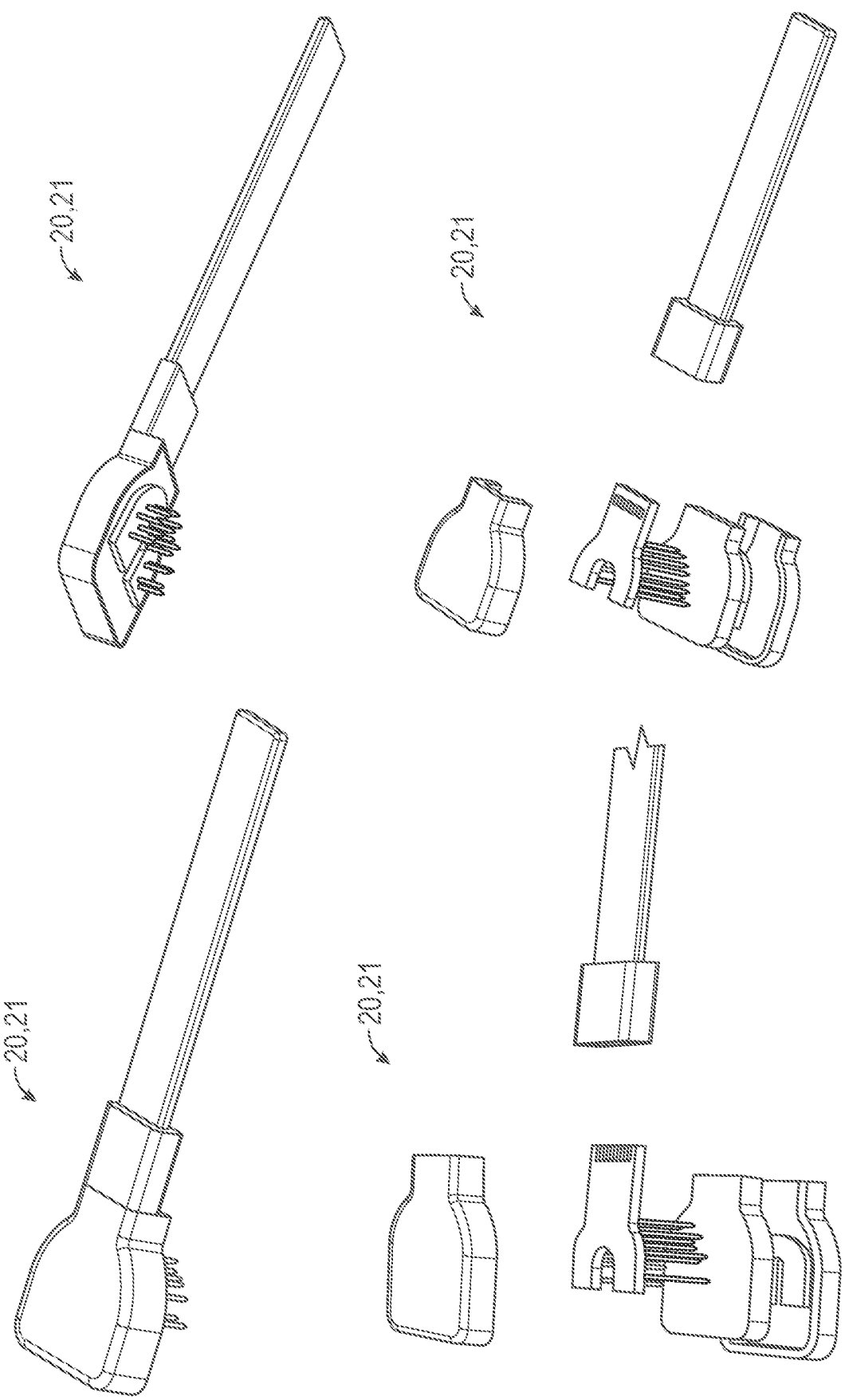
FIG. 2F are pictures of an electrode system that may be employed in the apparatus of FIG. 2A.

FIG. 2F are pictures of an electrode system that may be employed in the apparatus of FIG. 2A. In embodiments as shown, the needle arrays can be simply attached to a ribbon connector for manual application of the needles.

Figure 3A:
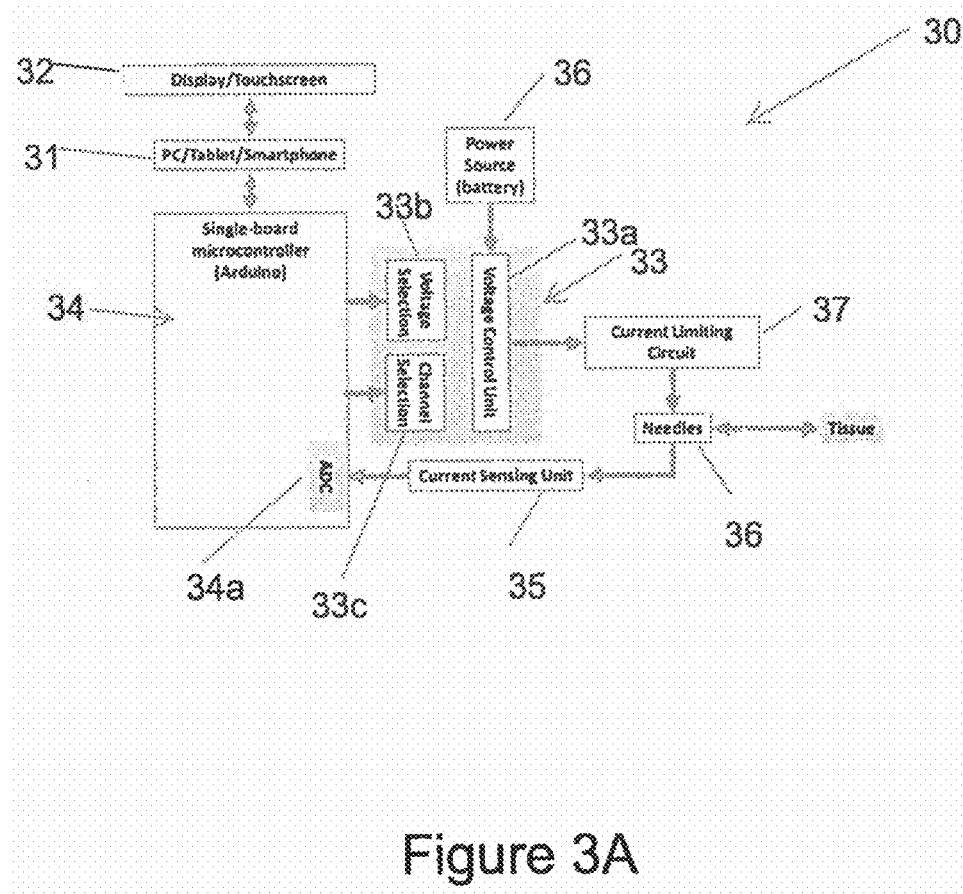
FIG. 3A is a block diagram of a system for ECT in accordance with an embodiment of the present invention.

FIG. 3A is a block diagram of an exemplary system for ELF in accordance with the present invention. According to this exemplary embodiment, a system 30 may include a computer 31 with a display 32, which can communicate with a controller 34. In turn, the controller 34 may control a circuit 33 that can include a voltage control unit 33a, a voltage selection unit 33b, and a channel selection unit 33c. For example, the voltage selection unit 33b may enable a user to select a voltage to be applied to a current limiting circuit 37 described below, while the channel selection unit 33c may enable the user to select one or more electrode pairs to be activated in the tissue.

The system 30 may further include a power source 36 may supply power, via the voltage control unit 33a, to a current limiting circuit 37. In turn, the current limiting circuit 37 can apply a potential across cathode and anode needles 36. A current sensing unit or circuit 35 can monitor the current across the needles and provide feedback information, via an analog to digital converter 34a, to the controller 34.

Though the foregoing example is described in the context of wired circuitry, the present invention contemplates that the same can be implemented in software.

Figure 3B:
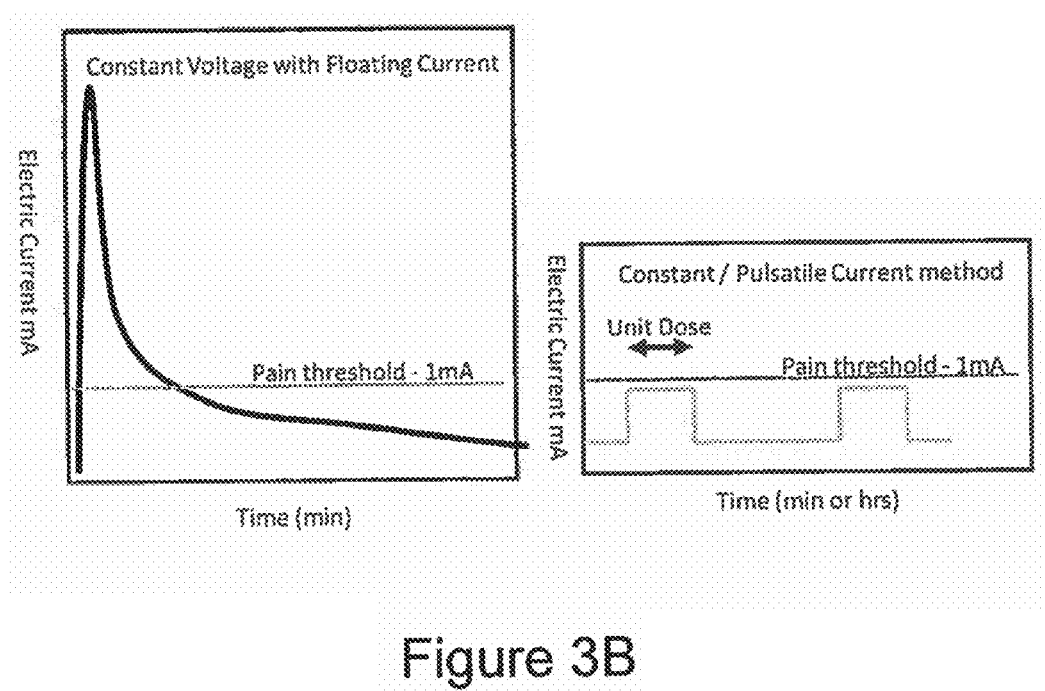
FIG. 3B are estimated graphs of current versus time that may be employed for the system in FIG. 3A.

FIG. 3B are estimated graphs of current versus time that may be employed for the system in FIG. 3A. The left graph is a depiction of ECT treatment of skin tissue when voltage is kept constant while current level is allowed to float. The right graph is a depiction of ECT treatment of skin tissue when electric current is set at a constant level or stepwise current is delivered.

Exact current traces may vary over a wide range as it depends on various factors such as the number of electrodes and their geometry, target tissue types and their hydration state, and presence or absence of electrolytes. It should be noted that if electric current is allowed to float, it may reach over 10 mA during the initial peak, which can cause extreme pain without appropriate anesthesia (local anesthetic injection). Impedance goes up during ECT treatment because water content goes down. And diffusion cannot sustain the delivery of new water molecules to fuel the reaction. Simple diffusion of water from surrounding area alone cannot maintain the localized water loss. As such, by applying an intermittent treatment dosage scheme rather than a long continuous one, resting period in between each treatment bolus may allow local hydration equilibrium to be re-established.

Generally, applying a fixed voltage while allowing free current draw into tissues causes pain. Pain perception due to electrical current can vary depending on application site, age, race, gender and BMI index, but a typical threshold for DC pain perception falls between 1 mA and 10 mA. To reduce or even eliminate possible pain and discomfort sensations, electric current during ECT treatment can be limited to about 1~2 mA or below. Likewise, local or regional anesthesia can be used to reduce or block pain as is the case in most dermatologic procedures.

In embodiments, reducing or eliminating current induced pain may be in the form of sequential treatments of step-wise direct current (DC) (FIG. 3B, right graph). By maintaining the electric current level below the pain threshold, one could apply either constant DC or sequential dosages of DC current to the tissues. Treatments can then be monitored for their exact dosage through time and can be applied in sequential fashion with intermittent healing period to allow chemical re-balancing in tissues and thus potentially reduce tissue damage due to over-treatment. A balanced dosimetry scheme can be developed with consideration of the current level applied, total electrical charge transfer needed per treatment session, and other factors such as needle configurations and tissue types.

Figure 3C:
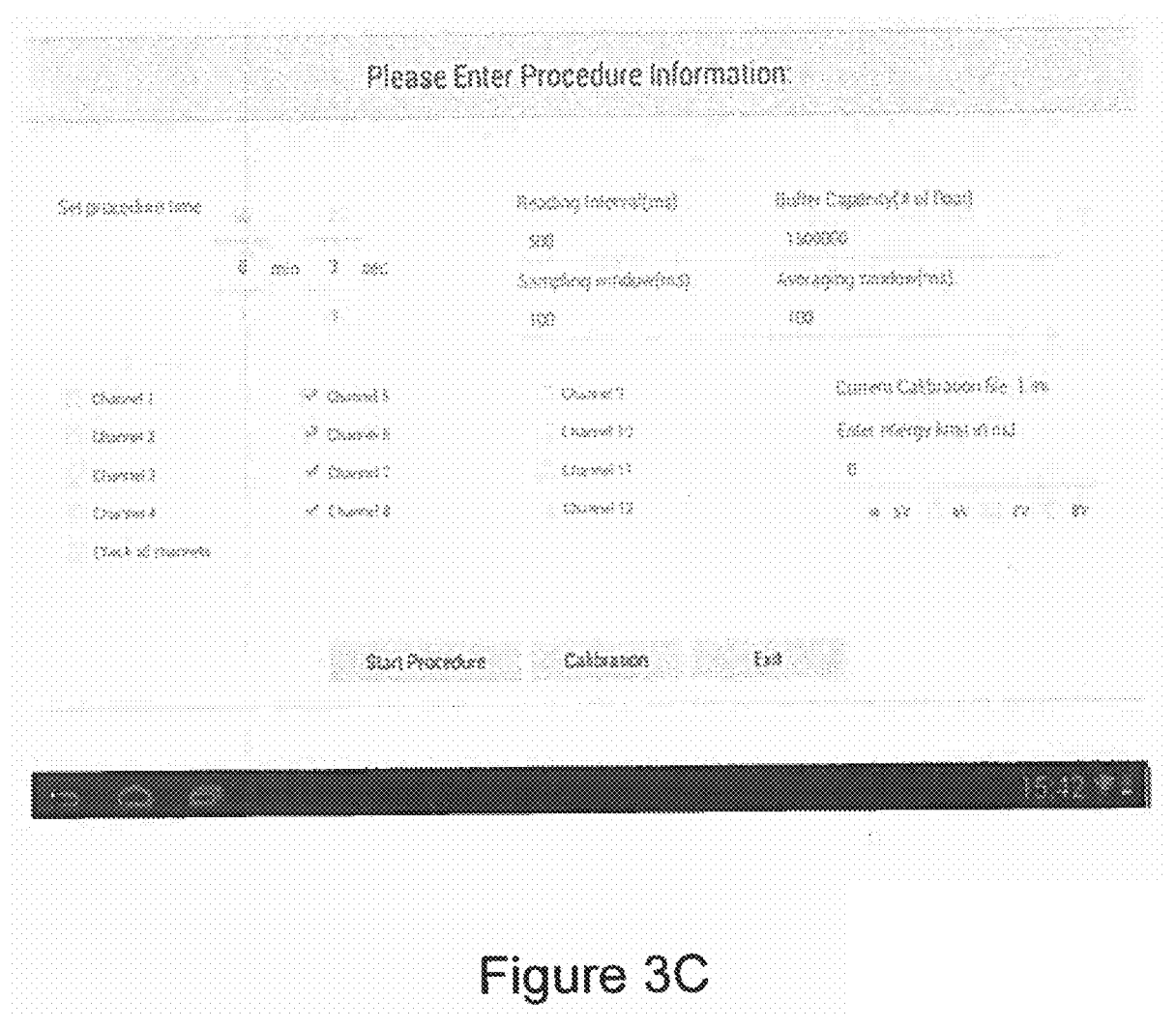

FIG. 3C is a screenshot of a user interface that may be part of the system in FIG. 3A.

Figure 3D:
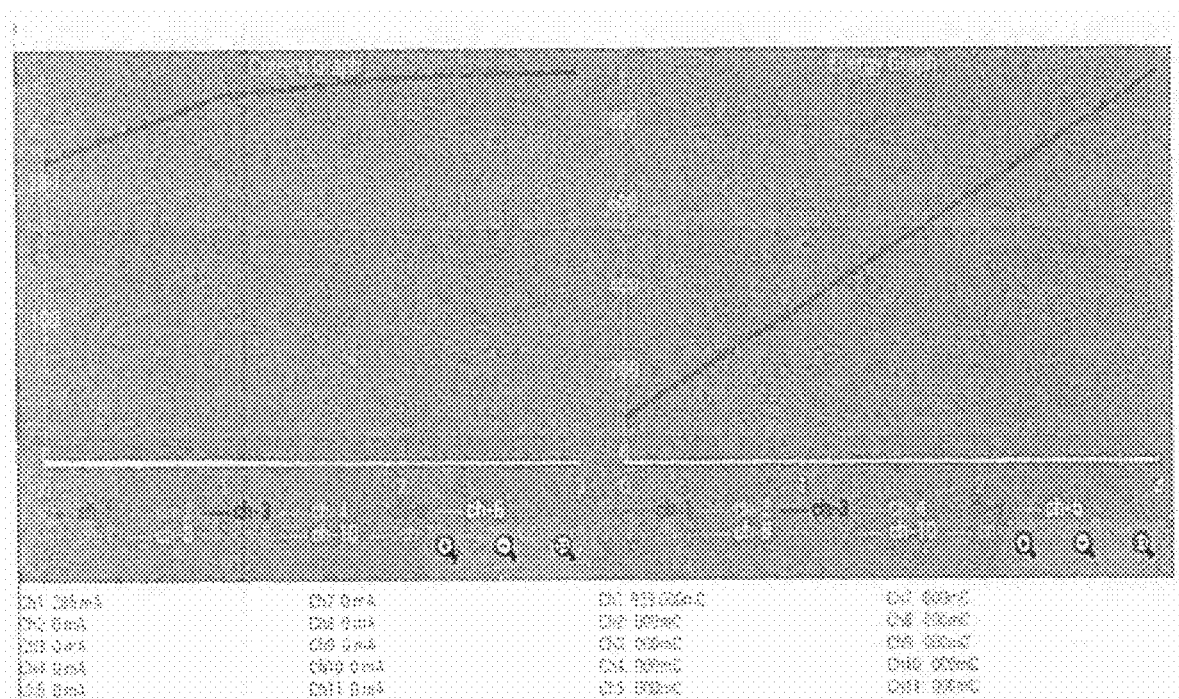
FIG. 3D are screenshots of graphs that may be part of the system in FIG. 3A.

FIG. 3D are screenshots of graphs of real-time monitoring of electric current per channel (left graph) and of total electric charge delivered per channel (right graph) that may be part of the system in FIG. 3A.

Implementation of the method, apparatus and system of the present invention can have numerous effects. In skin tissue, this can result in the breakdown of the cell membrane, as well as hydrolysis of the molecules themselves. High concentrations of both acid and base can have a major effect on skin tissue. The tissue effect can be spatially limited to the immediate vicinity of the electrodes because the interstitial fluids of the body are a heavily buffered system. The other factors governing the spatial limits of the tissue effects are the electric field gradient and the chemical gradient. Notably, as gas ($H_2$ and $O_2$) is evolved, this can form a natural and obvious contrast media which can be readily detected using ultrasound or similar imaging technologies. The combination of this electrochemical treatment with ultrasound imaging provides a means to monitor and feedback control the tissue effect. Likewise, dosimetry may be established using electrical feedback as well to monitor total charge delivery which directly relates to the amount of water electrolyzed.

The present invention can alter skin tissue by inserting a pair, array, or multiple needle electrodes into the target tissue. A low voltage with floating, constant or pulsed current can be delivered to the electrodes from a DC power source (such as a battery) or a potentiostat. With the electric field turned on, the electrolysis can be triggered and can generate acid and base molecules. Electrochemically produced acidic and basic species can then cause breakdown of skin cells and molecules. The process can be feedback controlled via a number of mechanisms including monitoring of charge transfer (current) and/or imaging. Imaging is important, as a byproduct of water electrolysis is molecular oxygen and hydrogen. These gases can create significant acoustic impedance changes in tissue. This can provide good contrast for ultrasonic imaging which can be used to directly monitor the spatial extent of tissue change.

In the present invention, the change to skin tissues can be both mechanical and electrochemical. The use of numerous needle arrays can create mechanical disruption followed by the electrochemical disruption and/or degradation from the generation of acid and base, all in a highly localized manner.

In the present invention, electrochemistry of biological tissues at low voltage (i.e., applied potentials of roughly ±2V vs. the normal hydrogen electrode) involves mainly water electrolysis at the tissue/solution interface. Electrolysis of saline solutions (or tissue fluids) generates sodium hydroxide and hydrogen gas at the negative electrode and chlorine gas, oxygen gas, or both at the positive electrode. Species generated do depend upon the potential as well as the electrode composition and electrical circuit design.

The skin breakdown process involving ECT according to the present invention can be attributed to the formation of acid/base species at the electrodes. For example, saponification or "soap production" involves hydrolysis of fat (triglycerides) with sodium hydroxide, which is generated at the negative electrode in this invention. The chlorine gas produced at the positive electrode rapidly converts to hypochlorous acid in aqueous solution. Sodium hypochlorite, commonly known as bleach, is known to degrade skin. In addition, sodium hypochlorite is highly reactive towards proteins and other biological molecules.

The ECT process of the present invention has unique advantages over the use of simple chemical methods, as the electrochemical treatment can be highly localized to needle tips by using needle electrodes with insulated shafts. Use of microneedle arrays may provide efficient treatments since the microneedles can create mechanical disruption of skin tissues followed by electrochemical disruption and/or degradation. In addition, the dosage scheme in ECT of the present invention can be controlled by needle configuration, voltage, and the total current delivered. Availability of multiple parameter control would then allow physicians to better fine-tune the treatments for best outcome. The ECT process of the present invention is not drug delivery and relies upon a medical device to alter the physiological milieu of skin tissue.

As disclosed herein, ECT can include one or more aspects of PDEMT. Accordingly, the present invention involves the role of electrical potential rather than voltage differences, as one can isolate and identify the precise electrochemical reactions that cause events such as shape change or tissue injury. Instead of applying a large voltage difference between two electrodes, the present invention can utilize an electrochemical potentiostat to apply a specific electrical potential to an array of electrodes where discrete electrochemical reactions can be isolated. Hence, reactions that favor specific biochemical change can be selected over those that cause non-specific tissue injury. The present invention can capitalize on the innate structure of skin tissue, where part of the shape-change process is related to the interplay between charged macromolecular matrix components (proteoglycans), free ions, water, and electrochemical reactions at the interface between tissue and electrode.

There are many different embodiments of the present invention that can deliver low voltage and current in DC form. A simple embodiment may be a DC battery source with a fixed voltage (e.g., 3-9 volt batteries) with floating current draw. However, there are disadvantages related to a constant voltage application with floating current as the changing current level during treatments make it difficult to predict the total amount of energy deposited into the target tissue. Total charge delivered to the tissue may be monitored for each electrode pair with changing current level. This embodiment, though functional, if applied to well nerved tissues such as skin can cause an extremely painful experience in the patient as the current can easily exceed the pain threshold of ~1 mA typically felt in an average adult. Thus, use of 'floating' current devices may require local nerve block or full anesthesia during ECT treatments. See FIG. 3B for a typical electric current profile during ECT, where the peak of the current can exceed over 10 mA for 1 Os of seconds.

Another embodiment of the ECT device may employ a current limiting circuit that will keep the electric current per needle pair to stay well below ~1 mA, which is the pain threshold for typical human adults. The low electric current level can be achieved with or without using parallel circuits for the needle pairs. For example, 5V current with 10 mA limit can be applied to 20 pairs of needles in parallel circuit to achieve approximately 0.5 mA maximum current reached for each pair of electrodes, given that tissue resistance does not vary widely across the electrodes. The active resistance of the tissue may increase with increasing electrical charge deposition over time, and may vary by location. This, in turn, can potentially create uneven current level among the parallel electrode needle channels. For this reason, it can be important to monitor the electrical current at each channel to avoid over- or under-treatment in the tissue.

Another embodiment may include an independent circuit design to achieve constant electrical current for each channel for a dedicated electrode pair. For example, each independent channel can control and monitor a single pair of needle electrodes. Each channel may be controlled for different voltages and maximum current levels. FIG. 3A is an example of an embodiment of an ECT device that can control voltage, current level via a pre-programmed control unit. The needles can be controlled via a single channel or multichannel unit. Each channel can control and monitor a single pair of electrodes (cathode/anode) or multiple pairs or other configurations where the number of cathodes are different from the number of anodes.

In some embodiments, the settings and electrical dosage can be monitored via a graphical user interface on a computing unit such as smartphones, tablets and computers (See FIGS. 3C and 3D).

In some embodiments, one can apply step-wise electrical doses with an exact amount of pre-defined current level and thus the total electrical charge delivered is directly proportional to the time period of unit dose and the total number of doses. (See FIG. 3B). One advantage of this method is that current monitoring may not be necessary. Another advantage of this type of "constant" current step-wise dosing is that one can apply an intermittent treatment scheme. For each unit dose, one can apply the maximum dosage that can be tolerated by the tissue without causing permanent or irreparable tissue damage. An intermittent approach can provide a "healing" period (or time to allow electrochemical equilibrium) in between doses and minimize tissue damage while achieving electrochemical modification that leads to tissue regeneration. In this "intermittent" dosage scheme, the treating physician may control five different parameters to achieve optimal outcome of electrochemical modification while minimizing the side-effects: voltage level, current level, unit dosage time, frequency, and total number of unit dosage. This intermittent treatment concept can be extended from seconds, minutes, hours, or even days depending on the extent of the tissue modification required and patients' health and tolerance to treatments.

In light of the low-dose treatment procedure afforded by the low-current method, some embodiments of ECT can be in a form of a wearable device, with which a patient can apply the treatments to the target skin area at a medical office under a provider's supervision and also potentially at home. The total dosage may be planned and pre-programmed by a health practitioner. Also, the treatments can be incremental to allow possibly self-treatments without medical supervision. In this consumer health device embodiment, the maximum allowed doses must be restricted in order to prevent accidental or intentional over-treatments of tissues by users. In this and other embodiments, the needle applicators may be large enough to cover a relative large area (e.g., burn forearm, wrinkles in necks, etc.) unlike a small array described in this application. At home or at a medical office environment, topical anesthetics and/or antibacterial cream may be applied onto the treatment area prior/post to the treatments to avoid infections. The needle patches may be made to be one-time use disposable or re-useable with proper cleaning procedure.

In some embodiments, maintaining constant current may require floating the voltage over a wide range. In this case, the voltage must be above the threshold level that will induce electrochemical reactions inside skin and other connective tissues, typically 4-6V, but may vary depending on the tissue type (hydration, collagen density, etc). Also, it must stay below the voltage level that may cause excessive muscle contraction caused by electro-stimulation.

In some embodiments, needle electrodes may be hollow to allow injection of drugs that may enhance or moderate the electrochemical reactivity in the skin. For example, steroids may be injected to reduce inflammation (redness and swelling).

In some embodiments, an electric field may be applied to induce localization of particular drugs or chemicals rather than relying on simple diffusion dominated processes. This may be used not only in skin applications but other connective tissues (i.e., articular cartilage) where drug diffusion may be a limiting process. In this case, the electric field may be used to enhance the drug delivery process in combination with the electrochemical modifications.

In some embodiments, the spatial placement of the needle electrodes may be customized in such a way that electrochemical reactions are localized into a specific spot rather than applied evenly over the target tissue area. (See FIG. 2D).

In some embodiments, the electrodes may be a mix of transcutaneous needle electrodes and contact patch electrodes.

In some embodiments, a galvanostat or potentiostat design can be implemented to reduce localized electrochemical reactions at the surface of electrode while inducing electric field gradient inside the target tissue zone.

In some embodiments, the needle array and applicator for needle array can be pushed mechanically or by hand.

In some embodiments, the needle penetration is achieved through an electromechanical motor or motion actuator with precise depth control.

In some embodiments, the needle arrays can be designed as disposable units with the array unit being mounted inside a cylindrical tube for mechanical actuation (see FIG. 2E), or they can be simply attached to a ribbon connector for manual application of the needles (see FIG. 2F).

In some embodiments, the needles can be insulated on the shaft to induce electrochemical reactions at a specified depth from the tissue surface (see FIG. 2B). The conductive part of the needle can be at one or multiple positions along the needle shaft, whose configuration can be used to control electric charge dosing at various target depths of the tissue.

Some embodiments may use computer and/or a tablet for graphic user interface which includes such functions as experimental control settings, real-time current graphs, and data recording.

In many embodiments, monitoring and feedback control process is important. For example, total charge transfer to each needle can be monitored. Other monitoring methods may be applied. For example, optical methods can be used to monitor and provide feedback control as well. Potentially, fiber optics can deliver and collect light in the vicinity of needles and be used to monitor the progression of therapy. Ultrasound imaging may be used to monitor changes in collagen density and structure within the tissue before/during/after electrochemical reactions have been performed. Optical coherence tomography may be used to monitor the depth of wide spread effect into the tissue before/during/after electrochemical reactions have been performed In one embodiment, the present invention provides a method of shaping skin tissue by using a minimally invasive, needle based approach. As further described herein, in one embodiment, a potentiostat is incorporated to control potential rather than simply applying a voltage difference. This can overcome a significant limitation in that specific chemical reactions can be used for therapy and while others are rejected.

In one embodiment, the incorporation of potentiostat technology is used to select specific electrochemical potentials to isolate specific chemical reactions. In another embodiment, the present invention is used to choose between one anodic and/or cathodic half-reaction thereby potentially enhancing/diminishing undesirable outcomes. In another embodiment, the incorporation of a potentiostat is used for multiple tissue electrodes. In another embodiment, the present invention is used to contain and/or localize undesirable half-reactions to a site distal to tissue of interest (even with the use of a sacrificial electrolyte outside the tissue).

In one embodiment, the technology allows for the use of chemically modified electrodes to further select specific electrochemical reactions to optimize shape and mechanical properties change/minimize tissue damage. The potentiostat can operate in modes where a constant voltage is applied, a constant current is applied, operating in galvanostatic mode, or a pulsed, alternating, or ramped application of voltage or current is used to optimize the concentrations of electrochemically generated species that affect tissue shape change. In another embodiment, the amount of electric charge transferred through each electrode of the potential-driven electrochemical modification of tissue (PDEMT) system is monitored and controlled by switching on/off individual electrodes and controlling applied voltage/current.

In other embodiments, the present invention provides a method of shaping skin tissue in a patient, comprising providing a potential-driven electrochemical modification of tissue (PDEMT) device, and using the PDEMT device to shape skin tissue in the patient. In another embodiment, skin tissue is shaped by water hydrolysis that results in protonation of fixed negative charges. In another embodiment, the invention further comprises increasing tissue viability by minimizing pH gradients and/or ROS generation. In another embodiment, the device incorporates bipotentiostat and/or polypotentiostat technology.

Other embodiments include a method of treating a skin tissue condition in a patient, comprising providing a potential-driven electrochemical modification of tissue (PDEMT) device, and treating the patient by using the PDEMT device to shape skin tissue. In another embodiment, the device incorporates bipotentiostat and/or polypotentiostat technology.

Other embodiments include an apparatus, comprising a potential-driven electrochemical modification of tissue (PDEMT) device adapted for shaping skin tissue in a patient. In another embodiment, the device incorporates bipotentiostat and/or polypotentiostat technology.

In another embodiment, general surgical or medical device technology may be used to deliver electrical charge or energy to skin tissue to create in situ electrochemical reactions. In another embodiment, the present invention provides use of electrochemistry to control and generate specific user defined chemical reactions in regions defined by electrode placement and geometry. In another embodiment, the invention provides species (agent) selectivity and/or spatial selectivity. As readily apparent to one of skill in the art, a variety of treatments and applications to skin tissue that require control and optimization may be used in conjunction with various embodiments herein. For example, interactions created can result in the modification of a target tissue for medical therapeutic effects including, change in physical properties (such as mechanical behavior—static and dynamic, electrical behavior, optical properties, or thermal properties), or changes in biologic behavior (such as cell injury, cell death, cancer treatment, cell proliferation, shape change of tissue, appearance of tissue, alter drug delivery properties of tissue). Or, for example, it may be performed in tandem with user imposed or defined changes in mechanical state in tissue (user defined stress-strain), temperature of tissue (heated or cooled), pressure/compression (internal stress), or atmospheric and ambient conditions.

As further described herein, in one embodiment, the present invention provides for a system that controls the process of current delivery or potential application. In another embodiment, the system has several electrodes including working, reference, and auxiliary, or cathode and anode. These electrodes can be placed into tissue in varying geometric arrangements. In another embodiment, there may be more than one of each of these types of electrodes within a therapeutic system. As apparent to one of skill in the art, any number of electrode shapes and materials are readily available and may be used in conjunction with various embodiments herein. For example, the electrode can be static or within a flow through cell, or in the shape of needles, flat plates, complex shapes (such as curves, or clamshell), screens, foams, solid-stiff, soft, pliant, moldable, conforming, or liquid (such as mercury, and other alloys).

Or, for example, electrodes could be made of platinum, iridium, graphite, coated with oxidation catalysts, sequestered auxiliary electrodes in an isolated chamber connected by a salt bridge or Luggin capillary, reference electrode, or composed of base metals and electro-plated. Similarly, the electrodes may be placed in any number of useful geometric arrangements. For example, in one embodiment, cathode and anode electrodes may be placed within the tissue in either close proximity or at a distance from one another. Or, in another embodiment, an array of electrodes may be fashioned to cover a large or unique region of interest. In another embodiment, the reference electrode may not interact directly with tissue of interest (e.g., separated by a Luggin capillary or salt bridge). In another embodiment, the auxiliary electrode may not interact directly with tissue of interest (e.g., separated by a Luggin capillary or salt bridge). In another embodiment, the electrical current, charge transfer, and/or potential are modulated. In another embodiment, modulation includes pulsed, complex or simple waveform, and/or on and off cycles. In accordance with various embodiments herein, more than one system or set of electrodes can be used, which can include simultaneously or at different times, or at the same location or spaced apart with variable or constant distances, or multiplexing of the specific chemical reaction desired.

As further disclosed herein, the system that controls the process of current delivery or potential application may also include one or more control system instrumentations. As readily apparent to one of skill in the art, there are a variety of available devices and systems that may be used to provide control instrumentation, as well as any number of elements that may be desired to be monitored and controlled in accordance with various embodiments herein. In one embodiment, the control system instrumentation is a potentiostatic control. In another embodiment, potentiostat includes bipotentiostats. In another embodiment, the potential is specified by the user. In another embodiment, the control system is a galvanostatic control, where the user can specify certain amounts of current, and potential will be set to establish that current. In another embodiment, simple operation amplifiers can function to accomplish the task of a potentiostatic and/or galvanostatic control. In another embodiment, the system further includes a feedback control. This may include control of tissue effect, where biophysical change can be monitored and information used to control current and/or potential. Or, for example feedback control may include monitored variables that include mechanical properties, electrical properties, and optical properties. In another embodiment, total charge transfer is also monitored. In accordance with various embodiments herein, control system instrumentation may be used to measure and/or control one or more of the following: current, potential, charge transfer, pH, concentration of various species generated by the device, and/or the evolution of gases.

In another embodiment, the device is designed for use in air and in aqueous environments, combined with image guided therapies to target specific tissues/targets, or perform simultaneous functions such as biopsy and tissue sampling. In accordance with various embodiments herein, the device may be used in tandem with one or more agents that activate a pro-genic drug (e.g., tumorcidal). This may include, for example, reactive oxygen specifies, generate in situ species, or the circumstance where the drug is activated only in vicinity of appropriate/extreme user defined electrical potential. Defined electrical potential may include, for example, creating spatial selectivity based electric field, or isolate deleterious or desired reaction to what is defined by electrode placement geometry. In accordance with various embodiments herein, the device may be used in tandem with user created changes in tissue composition, injectable drugs, agents that produce cross-linking of proteins, agents that alter pH, or activate a catalyst for tissue effects including glue, tumorcidal, or mechanical property change, etc. Similarly, the device may be used in tandem with one or more of the following: osmotically active agents, saline solutions (hyper and hypotonic), buffers, reactive oxygen scavengers, and other chemicals that change or alter electrochemistry of the system.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the selection of constituent modules for the inventive compositions, and the diseases and other clinical conditions that may be diagnosed, prognosed or treated therewith. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

It is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Overview

In one embodiment, potential driven electrochemical modification of tissue (PDEMT) is a technology that can be used to create discrete electrochemical reactions in tissue. In one embodiment, a potentiostat is employed to select and control the specific electrochemical reactions that occur at an electrode-tissue interface. A potentiostat is the electronic hardware based upon operational amplifiers or other non-linear electrical circuits, and is required to control a three electrode cell and run most electroanalytical experiments. A bipotentiostat and polypotentiostat are potentiostats capable of controlling two working electrodes and more than two working electrodes, respectively. PDEMT implicitly is a new treatment modality that relies upon control of redox chemistry. Redox reactions, or oxidation-reduction reactions, have a number of similarities to acid-base reactions. Like acid-base reactions, redox reactions are a matched set, that is, there cannot be an oxidation reaction without a reduction reaction happening simultaneously. The oxidation alone and the reduction alone are each called a half-reaction, because two half-reactions always occur together to form a whole reaction. When writing half-reactions, the gained or lost electrons are typically included explicitly in order that the half-reaction be balanced with respect to electric charge. A potentiostat allows the separation of the two half-reactions spatially which is important, as in living tissues the major redox reaction that occurs with PDEMT is the electrolysis of water. Complex species may be generated with hydrolysis and PDEMT permits a means to isolate desirable reactions and reduce or eliminate those which are deleterious.

Example 2

Incorporation of Potentiostat Technology

The incorporation of potentiostat technology can be important in implementation of this technology as one may a) select specific electrochemical potentials to isolate specific chemical reactions; b) choose between one anodic and/or cathodic half-reaction thereby potentially enhancing/diminishing undesirable outcomes; c) use multiple tissue electrodes; and d) potential to contain/localize undesirable half-reactions to a site distal to the tissue of interest (even with the use of a sacrificial electrolyte outside the body, tissue, or organ). The technology additionally allows for the use of chemically modified electrodes to further select specific electrochemical reactions to optimize shape and mechanical properties change/minimize tissue damage. The potentiostat can operate in modes where a constant voltage is applied, a constant current is applied (operating in galvanostatic mode), or a pulsed, alternating, or ramped application of voltage or current is used to optimize the concentrations of electrochemically generated species that affect tissue shape change. In addition, the amount of electric charge transferred through each electrode of the bi-/multipotentiostat PDEMT system can be monitored and controlled by switching on/off individual electrodes and controlling applied voltage/current.

Example 3

Figure 4A:
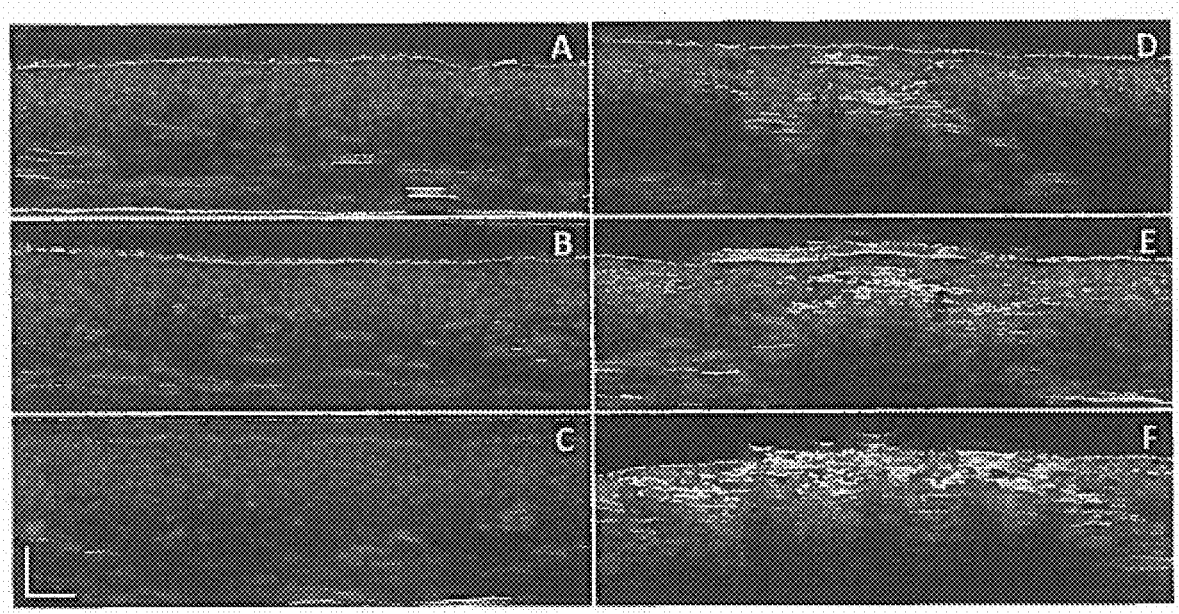
FIG. 4A are ultrasound images depicting the effects of ECT in accordance with embodiments of the present invention.

FIG. 4A are ultrasound images depicting the effects of ECT in accordance with embodiments of the present invention:

Image A is of a normal control human skin in phosphate-buffered saline (PBS).

Image B is human skin submersed in 1× acetic acid for 45 minutes.

Image C is human skin submersed in 1× sodium hydroxide for 45 minutes.

Image D is human skin after 4V for 3 minutes of ECT with anode and cathode 2 mm separation.

Image E is human skin after 5V for 3 minutes of ECT with anode and cathode 2 mm separation.

Image F is human skin after 4V for 3 minutes of ECT with anode and cathode 2 mm separation.

In Images A and B, the epidermis and dermis are both unaffected.

In Image C, the epidermis has been eroded as indicated by a decrease in signal intensity.

In Image D, a conically shaped affected area can be observed underneath the epidermis, travelling down to the subcutaneous tissue.

In Image E, the affected area is more widespread and prominent, in addition to the epidermis increasing in signal intensity due to an impedance mismatch.

In Image F, the affected region caused by the needle array shows the complete change in epidermal and dermal tissue.

Example 4

Figures 4B, 4C:
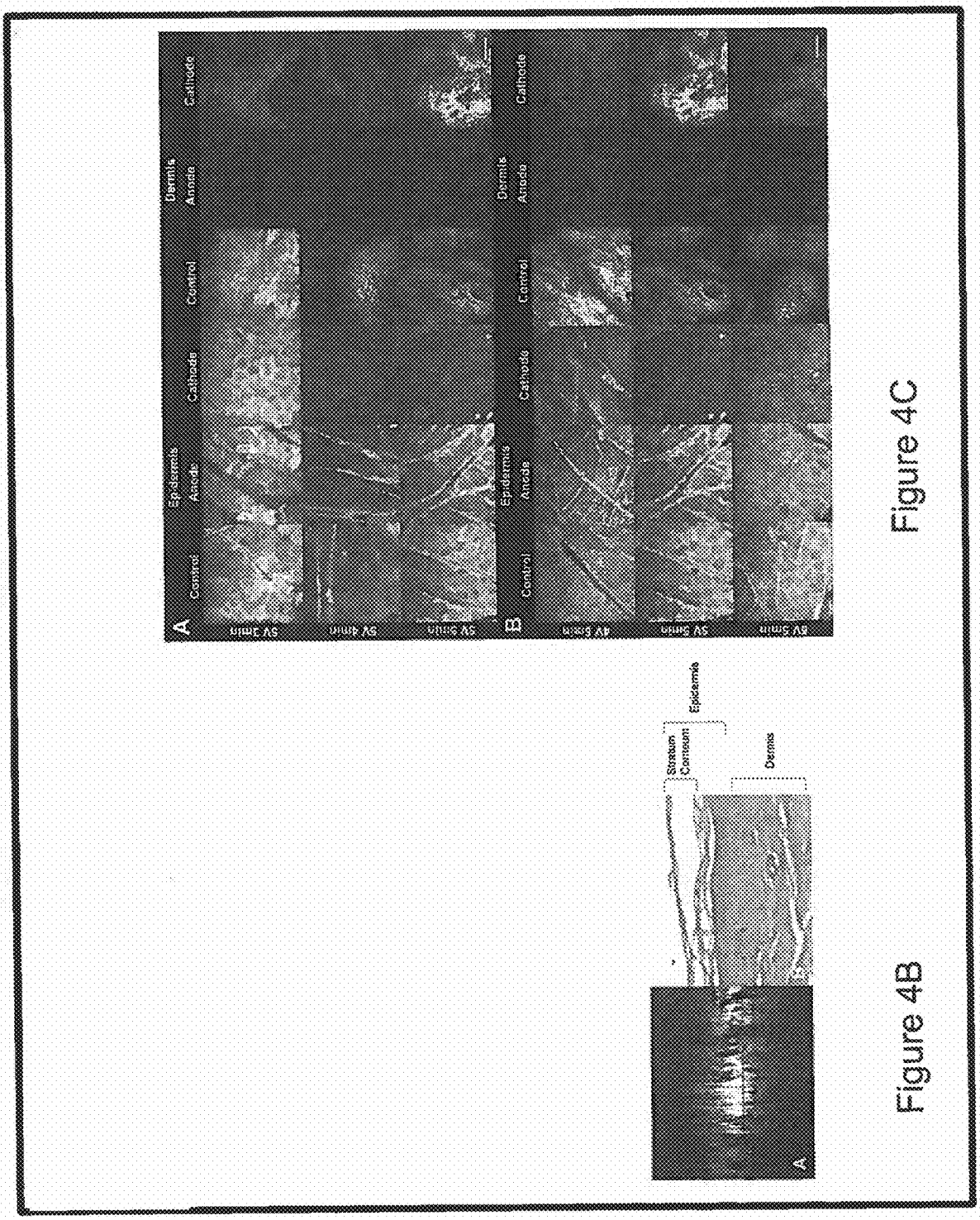
FIG. 4B are multiphoton microscopy and stain images of tissue prior to ECT.
FIG. 4C are multiphoton microscopy images of tissue after ECT in accordance with embodiments of the present invention.

FIG. 4B are ex vivo multiphoton microscopy (MPM) image (A) and hematoxylin and eosin stain image (b) of normal human skin prior to ECT treatment. Multiphoton microscopy is a laser-scanning microscopy technique that produces high resolution images using non-linear light-matter interactions such as two-photon excited fluorescence (TPEF) and second harmonic generation (SHG). SHG is used to visualize collagen fibers in the dermis.

FIG. 4C are ex vivo MPM images of normal human skin following ECT treatment at 10×. Horizontal optical sections (XY scans) show keratinocytes in the epidermis at z=25 μm, and collagen in the dermis at z=100 μm. Scale bar is 50 μm for all MPM images. Images A are ECT treatment at constant voltage with increasing time. Images B are ECT treatment at increasing voltage with constant time.

Example 5

Figure 4D:
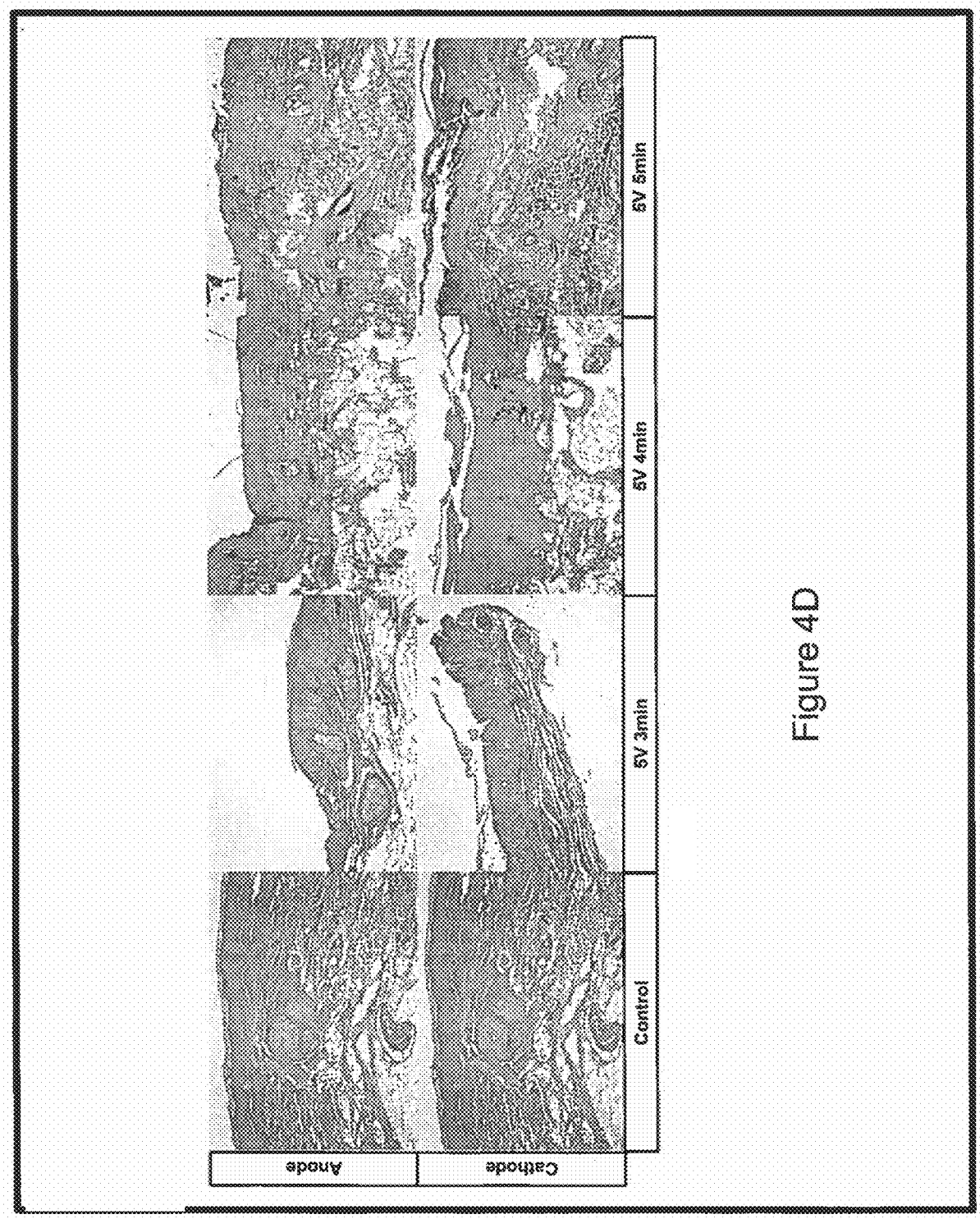
FIG. 4D stain images of tissue before and after ECT in accordance with embodiments of the present invention.

FIG. 4D are hematoxylin and eosin stain images at 4× of ex vivo human skin without ECT treatment and with ECT treatment at constant voltage (5V) and increasing time (min).

Example 6

FIG. 5 are pictures of ex vivo pH application of normal human skin following ECT treatment. Images A-B are cross-sectional views (XZ cut) through both platinum needle insertion sites. Scale bar is 1 cm in all images. Images A are ECT treatment at constant voltage (5V) with increasing time (min). Images B are ECT treatment at increasing voltage (V) with constant time (5 min). Images C is a universal indicator pH test chart.

Example 7

FIG. 6 are graphs of mean ECT effect (mm) of normal human skin. Graph A is mean base width at constant voltage (5) and increasing time (min). Graph B is mean acid width at constant voltage (5V) and increasing time (min). Graph C is mean base width at increasing voltage (V) and constant time (5 min). Graph D is mean acid width at increasing voltage (V) and constant time (5 min).

The graphs show increasing mean width with either increasing voltage or increasing time.

Example 8

FIG. 7 are graphs of mean ECT effect (mm) of normal human skin±SD at constant voltage (5V) at increasing time (min); n=5 for 3 min, n=6 for 4 min, and n=6 for 5 min. Graph A is for the mean base width. Graph B is for the mean acid width.

Graphs A and B show increasing mean width with increasing time.

Example 9

Figures 8, 9:
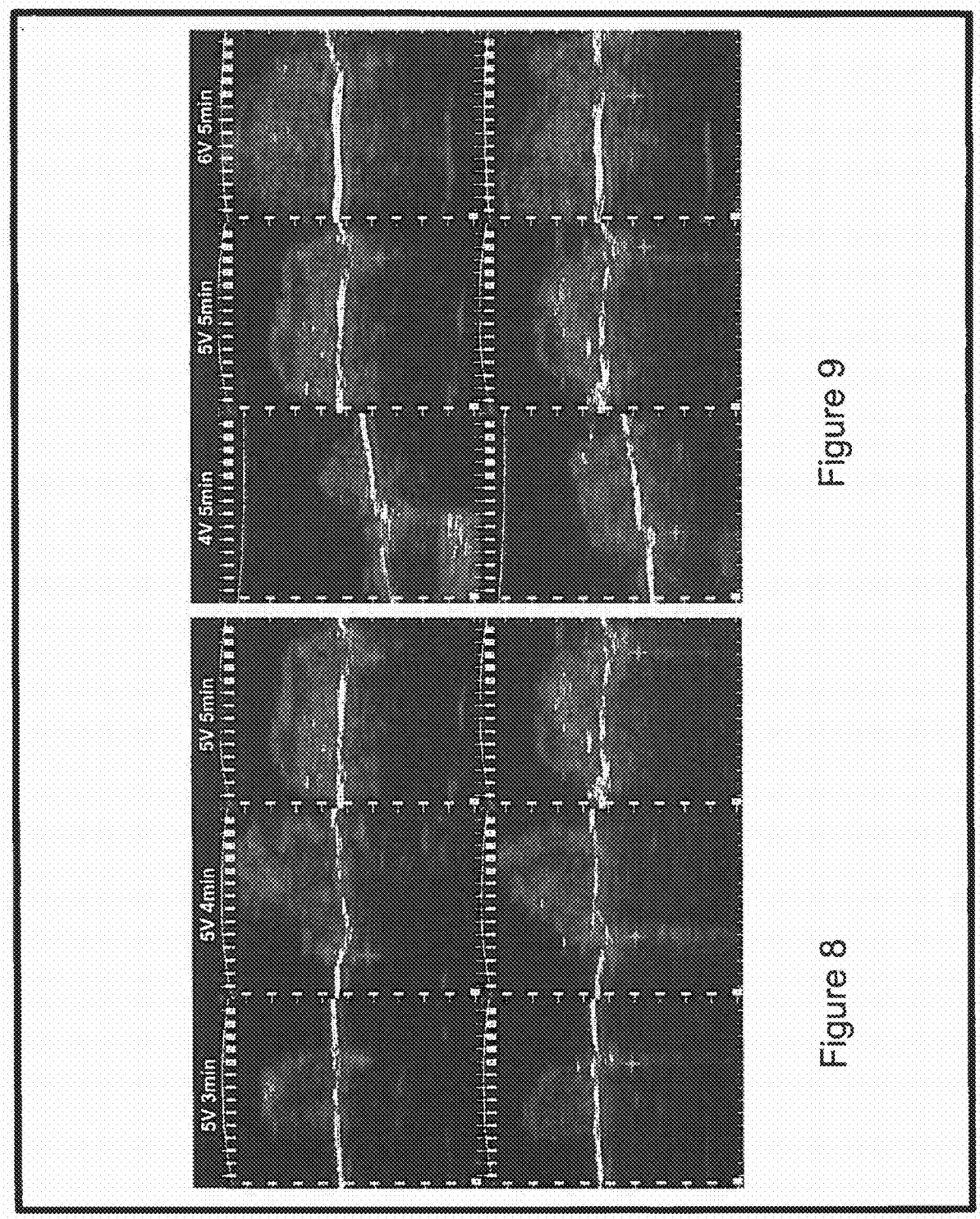
FIG. 8 are ultrasound images of tissue after ECT in accordance with embodiments of the present invention.
FIG. 9 are ultrasound images of tissue after ECT in accordance with embodiments of the present invention.

FIG. 8 are ultrasound (25 MHz) images of normal human skin following ECT. Cathode signal and anode signal are both at constant voltage (5V) and increasing time (min).

FIG. 9 are ultrasound (25 MHz) images of normal human skin following ECT. Cathode signal and anode signal are both at increasing voltage (5V) and constant time (min).

Conclusions

Potential-driven electrochemical modification of tissue (PDEMT) can be used to alter the mechanical structure of skin tissue. Using this technology, tissue can be stretched, shortened, bended, curved, strengthened, and weakened. Also, this technology can be used to focally create electrochemical changes locally in tissue as well. This technology creates electrochemical changes in tissue using a unique means to control the delivery of electrical energy and create specific user-defined electrochemical reactions in localized or diffuse regions in the tissue. The technology allows separation of anodic and cathodic redox chemistry reactions to distinct sites that may be adjacent to one another or separated spatially. This invention relies upon principles of electrochemistry to alter the complex chemical milieu in skin tissue to achieve structural changes and macromolecular alters in the matrix.

Conventional surgery requires skin incisions, almost always general anesthesia, longer operative times and recovery, and additional loss of time from work. The present inventive techniques are well suited to alter the shape of native tissue, and minimally invasive needle-based techniques could be used for in the office under local or regional anesthesia.

ECT does not rely upon and avoids or minimizes the potential for resistive heat generation, and exploits the molecular properties of the skin tissue to alter its mechanical state in response to changes in the electrical and chemical milieu that interacts with its charged tissue matrix. ECT is an ultra-low cost, needle-based therapy that can be implemented using only local anesthetics in most applications, and is suitable for office-based procedures. It represents a paradigm shift in that only electrochemical interactions in tissue are exploited to alter the material properties of proteoglycan tissues, leading to a safe approach to tissue reshaping. ECT represents a significant move away from "cut and suture" surgery toward in situ techniques that exploit precisely controlled chemical reactions to restructure tissue at the molecular level. In addition to the simple needle electrodes and power supplies (e.g., disposable batteries) used for ECT may also include an operational amplifier-based circuit for the application of a controlled potential. Thus, ECT is low cost and amenable to single-use applications (disposable components); indeed, because the potentiostat can be computer controlled, algorithms for the optimal ECT conditions can be pre-programmed into the clinical device to reduce the reliance of good surgical outcome on the individual surgeon's technical skill, much in the model of LASIK cornea reshaping (albeit at a minute fraction of the cost).

Because ECT is, at the molecular level, a consequence of electrode-driven chemical reactions, it builds upon a knowledge base derived from nearly a century of chemistry research in electrochemical processes. That basic research has played key roles in developing industrial technologies ranging from the lithium-ion battery to personal glucose monitors. It is notable that both major professional electrochemical societies—the International Society of Electrochemistry (ISE) and the Electrochemical Society (ECS)—have formal divisions in bioelectrochemistry, yet those divisions focus largely on the electrochemical properties of individual biomolecules (proteins and DNA), or on the development of electrochemical assays for drug metabolites and other molecular markers. The application of modern electroanalytical methods to investigate the effects of electrochemical reactions on macroscopic tissue is virtually unheard of, and offers an innovative model at the interface of basic chemistry, biomedical engineering, and medicine. ECT has the potential to revolutionize the reshaping and/or treatment of skin tissue.

The inventors have studied the molecular basis of ECT: most notably, they have established that ECT depends on specific electrochemical reactions at the tissue/solution interface, and examined the role of electrical potential. With the molecular mechanism(s) of ECT fully characterized, the application of electric fields using ECT may be tailored to select the specific reactions that create shape change while minimizing (or even eliminating) the reactions that cause tissue damage and cell morbidity.

Understanding the underlying molecular mechanism(s) of ECT is important to commercializing the reshaping process. Although several possible mechanisms may play a role (e.g., non-Faradaic protein and/or ion migration through the tissue caused by applied voltage gradients), the inventors' work supports that the dominant pathway involves water electrolysis and acidification at the tissue/solution interface. Over the voltage ranges examined in the inventors' previous studies, water and chloride are the main species that undergo redox chemistry.

Because pH staining is independent of the specific ECT protocol used, it can provide useful feedback data to alter and refine the p-EMR electrolysis conditions—for example, by applying different electrolysis waveforms (AC vs. DC). Electrochemical pH sensors based on ultra-microelectrodes inserted into the tissue (using the pH dependence of hydrogen evolution under galvanostatic control as the reporting element) may also be engineered, or using fiber-optic pH probes.

If chloride oxidation limits tissue viability, one might use alternative electrode materials for ECT. For example, $IrO_2$ has been identified as one of the best surfaces to carry out the 4e− oxidation of water as it can move the potential threshold from our empirical value of ~1.6 V vs. AgCl/Ag at platinum to near the thermodynamic value, ~0.75 V vs. AgCl/Ag—which is nearly ½ volt negative of the chloride potential. This would effectively eliminate both ROS production and chloride oxidation.

As shape change comes at the expense of cell injury, the optimization may require identification and selection of the appropriate applied potential (V), duration (t), electrode composition, and needle electrode placement. Combinations of these parameters determine resultant shape change, mechanical stability and tissue viability in a specimen, which are the clinically relevant factors to the reconstructive surgeon. In sum, the present invention may provide the following advantages:

Cost of the device is much less expensive than other energy-based skin therapies as it relies on low voltage power source Compared to the RF or laser-based techniques, the injuries can be delivered in slow fashion to ensure low-grade tissue injuries High spatial selectivity as determined by electrode design and composition, electric field geometry, applied potential, and current waveform In comparison to the simple needle array treatments, it affords better spatial selectivity in targeting both specific depth and region between needles. Specific depth targeted therapy can be accomplished better than simple micro-needle treatment alone.

Fewer and/or smaller needles can be used than in the simple micro-needle treatment while achieving the same effects as increasing the electrochemical dosage will expand the effective tissue injury volume Spatial selectivity is achieved through several routes, including needle electrical design, electrical dosimetry, selection of type chemical reaction, and the spatial placement of needles.

Side effects are expected much less than other energy-based thermal skin therapies as it creates subtle microscopic tissue damages rather than non-specific diffuse 'burns'.

Electrochemical alteration of dense collagen structures may enable improved injection, diffusion or localization of drug treatments through tissue modification when used in combination with drug treatments.

Intermittent treatments may enable repeated treatments by allowing healing period between treatments.

Spatial selectivity allows skin treatments that result in very subtle texture changes.

Both deep tissues and shallow tissues can be treated with different dosage through electrode configuration in both insulation zone depth and two-2 array As the lateral width of the tissue damage can be controlled via the electrical doses, one can use smaller diameters than those used in microneedling and RF-microneedles A relatively pain free procedure may enable 'wearable' devices for at-home treatments.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

It should be understood, of course, that the foregoing relates to exemplary embodiments of the invention and that modifications may be made without departing from the spirit and scope of the invention as set forth in the following claims.

We claim:

1. A method of altering skin tissue, comprising:
   creating an electrochemical reaction in the skin tissue with saline using an anode electrode and a cathode electrode;
   wherein the saline is a reagent in the electrochemical reaction in the skin tissue;
   wherein the electrochemical reaction occurs while avoiding thermal damage to the skin tissue.

2. The method of claim 1, further comprising providing feedback control of an electronic circuit connected to the anode and cathode electrodes.

3. The method of claim 2, wherein the electronic circuit is one of a potentiostat and a galvanostat.

4. The method of claim 1, further comprising altering a pH in the skin tissue.

5. The method of claim 1, further comprising placing at least one of the anode electrode and the cathode electrode in contact with the skin tissue.

6. The method of claim 5, wherein the placing the at least one of the anode electrode and the cathode electrode is in an absence of a voltage gradient across the skin tissue.

7. The method of claim 1, further comprising disrupting an ionic-bonding network in the skin tissue.

8. The method of claim 1, further comprising altering the skin tissue to a physiological pH after creating the electrochemical reaction.

9. The method of claim 1, further comprising limiting a change in the skin tissue temperature.

10. The method of claim 1, further comprising setting a concentration of electrochemically generated chemical agents, from the anode and cathode electrodes, that affect the skin tissue, by altering the electrochemical reaction at the anode and cathode electrodes.

11. The method of claim 1, wherein creating the electrochemical reaction includes employing potential-driven electrochemical modification of skin tissue (PDEMT).

12. The method of claim 1, further comprising:
   identifying and isolating at least one discrete electrochemical reaction that causes at least one of a shape change in the skin tissue, a change in the skin tissue mechanics, s change in the skin tissue viability, a change in the skin tissue matrix structure, and a change in the skin tissue composition.

13. The method of claim 1, further comprising changing at least one of a physical property and a biological behavior of the skin tissue.

14. The method of claim 13, wherein:
   changing the physical property of the skin tissue includes mechanical behavior—static or dynamic—electrical behavior, optical property, and/or thermal properties; and
   changing the biological behavior of the skin tissue includes tissue viability, matrix structure, and composition.

15. The method of claim 1, further comprising:
   placing the anode and cathode electrodes in a geometric arrangement in the skin tissue effective for altering the skin tissue.

16. A method of altering skin tissue, comprising:
   using at least one of an anodic electrode and a cathodic electrode in the skin tissue to initiate an electrochemical reaction in the skin tissue;
   using saline as a reagent in the electrochemical reaction;
   applying an electrical potential to the at least one of the anodic electrode and the cathodic electrode; and
   limiting a change in temperature of the skin tissue to avoid thermal damage to the tissue;
   whereby the saline undergoes electrolysis;
   whereby the electrochemical reaction alters the skin tissue.

17. The method of claim 16, wherein the method is carried out in absence of incising the skin tissue.

18. The method of claim 16, further comprising disrupting cell membranes of the skin tissue.

19. A method of altering skin tissue, comprising:
   mechanically disrupting the skin tissue;
   electrochemically degrading the skin tissue with an electrical potential applied to an anodic electrode and a cathodic electrode while in presence of saline used as a reagent which undergoes electrolysis during the electrochemically degrading; and
   minimizing a potential for thermal damage to the skin tissue.

20. The method of claim 19, wherein mechanically disrupting includes inserting the anodic and cathodic electrodes into the skin tissue.

21. A method of altering skin tissue, comprising:
   electrochemically generating sodium hydroxide, hydrogen gas, and either chlorine gas or oxygen gas in the skin tissue by applying an electrical potential to an anode-cathode pair and by electrolyzing a saline solution in the skin tissue;
   electrochemically forming acid/base species in the skin tissue, which forming alters the skin tissue; and limiting a temperature change of the skin tissue during electrochemically generating and electrochemically forming;
wherein applying the electrical potential is at a voltage not greater than 5V.

* * * * *